(12) United States Patent
Hergenrother et al.

(10) Patent No.: US 9,920,069 B2
(45) Date of Patent: Mar. 20, 2018

(54) COMPOUNDS FOR TREATMENT OF FLUOROQUINOLONE-RESISTANT BACTERIA

(71) Applicant: The Board of Trustees of the University of Illinois, Urbana, IL (US)

(72) Inventors: Paul J. Hergenrother, Champaign, IL (US); Elizabeth I. Parkinson, Champaign, IL (US); Joseph S. Bair, Millica Hill, NJ (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/126,786

(22) PCT Filed: Mar. 17, 2015

(86) PCT No.: PCT/US2015/021104
§ 371 (c)(1),
(2) Date: Sep. 16, 2016

(87) PCT Pub. No.: WO2015/142952
PCT Pub. Date: Sep. 24, 2015

(65) Prior Publication Data
US 2017/0096436 A1   Apr. 6, 2017

Related U.S. Application Data

(60) Provisional application No. 61/954,141, filed on Mar. 17, 2014.

(51) Int. Cl.
| | |
|---|---|
| *A61K 31/4748* | (2006.01) |
| *C07D 498/18* | (2006.01) |
| *C07D 498/16* | (2006.01) |
| *A61K 9/20* | (2006.01) |
| *A61K 9/48* | (2006.01) |
| *A61K 9/00* | (2006.01) |
| *A61K 9/12* | (2006.01) |
| *A61K 9/06* | (2006.01) |
| *A61K 31/4745* | (2006.01) |

(52) U.S. Cl.
CPC .......... *C07D 498/16* (2013.01); *A61K 9/0014* (2013.01); *A61K 9/0019* (2013.01); *A61K 9/06* (2013.01); *A61K 9/12* (2013.01); *A61K 9/20* (2013.01); *A61K 9/48* (2013.01); *A61K 31/4745* (2013.01)

(58) Field of Classification Search
CPC .......................... A61K 31/4748; C07D 498/18
USPC ........................................... 514/287; 546/64
See application file for complete search history.

(56) References Cited

U.S. PATENT DOCUMENTS

| | | |
|---|---|---|
| 4,692,452 A | 9/1987 | Cerny et al. |
| 5,716,963 A | 2/1998 | Lopez et al. |
| 2012/0258980 A1 | 10/2012 | Igarashi et al. |
| 2015/0011509 A1 | 1/2015 | Hergenrother et al. |
| 2015/0322033 A1 | 11/2015 | Hiramatsu et al. |
| 2016/0143878 A1 | 5/2016 | Hiramatsu et al. |
| 2016/0257651 A1 | 9/2016 | Hiramatsu et al. |

FOREIGN PATENT DOCUMENTS

| | | | | |
|---|---|---|---|---|
| EP | 2130831 A1 | 12/2009 | | |
| WO | WO 2015/006615 | * | 1/2015 | ............. A61K 31/40 |

OTHER PUBLICATIONS

Hiramatsu, K., et al., "Curing Bacteria of Antibiotic Resistance: Reverse Antibiotics, a Novel Class of Antibiotics in Nature; Int J Antimicrob Agents," 39(6):478-85; Jun. 2012.
International Search Report of the ISA/US dated Jul. 13, 2015; Int'l Application No. PCT/US2015/021104 filed May 9, 2014; Publication No. WO2015/142952 dated Nov. 13, 2014; 4pgs.
Perez, J.M., et al., "Concise Preparation of 1,8-Diazaanthracene-2,7,9,10-Tetraones. Two Alternative Syntheses of the Natural Antifolate Diazaquinomycin A," Tetrahedron; 56(26):4575-4583; Jun. 23, 2000.
Pettit, G.R., et al., "Antineoplastic Agents. 554. The Manitoba Bacterium *Streptomyces* sp.," J Nat Prod; 69(5):804-806; May 2006.
Written Opinion of the ISA/US dated Jul. 13, 2015; Int'l Application No. PCT/US2015/021104 filed May 9, 2014; Publication No. WO2015/142952 dated Nov. 13, 2014; 4pgs.

* cited by examiner

*Primary Examiner* — Charanjit Aulakh
(74) *Attorney, Agent, or Firm* — Haukaas Fortius PLLC; Michael H. Haukaas

(57) ABSTRACT

Compounds that specifically kill fluoroquinolone (FQ) resistant bacteria have been developed and are described herein. The FQs are the most commonly prescribed antibiotics to adults in the U.S. and thus are extremely important drugs. However, bacterial resistant to these drugs is now ubiquitous in some of the most common and deadly Gram-positive pathogens, including methicillin-resistant *Staphylococcus aureus* (MRSA) and vancomycin-resistant enterococci (VRE). Indeed, FQs are no longer indicated for treatment of MRSA and VRE infections because of such resistance. The compounds have specific and potent activity versus MRSA and VRE.

18 Claims, 17 Drawing Sheets

| FIG. 15A |
|----------|
| FIG. 15B |

TABLE 7. PRIMERS USED FOR SEQUENCING AND FOR SITE DIRECTED MUTAGENESIS.

| PRIMER | SEQUENCE | REFERENCE |
|---|---|---|
| ENTEROCOCCUS FAECALIS_gyrA_F | 5'-ATGAGTGAAGAAATTAAAGAAAACATTCA-3' | SATO, KENICHI ET. AL. ANTIMICROB. AGENTS CHEMOTHER. 2002, 46, 1800-1804 |
| ENTEROCOCCUS FAECALIS_gyrA_R | 5'-ACTCATACGTGCTTCGGTATAACGC-3' | SATO, KENICHI ET. AL. ANTIMICROB. AGENTS CHEMOTHER. 2002, 46, 1800-1804 |
| ENTEROCOCCUS FAECALIS_parC_F | 5'-GTGACAATTTTGGAAAAACGCCAAG-3' | SATO, KENICHI ET. AL. ANTIMICROB. AGENTS CHEMOTHER. 2002, 46, 1800-1804 |
| ENTEROCOCCUS FAECALIS_parC_R | 5'-CACCACTTAACTGTGATAAACGAGC-3' | SATO, KENICHI ET. AL. ANTIMICROB. AGENTS CHEMOTHER. 2002, 46, 1800-1804 |
| ENTEROCOCCUS FAECIUM_gyrA_F | 5'-CGGGGATGAACGAATTGGGTGTGA-3' | TORRES ET. AL. J. CHEMOTHERAPY. 2011, 23, 87-91 |
| ENTEROCOCCUS FAECIUM_gyrA_R | 5'-AATTTTACTCATACGTGCTTCGG-3' | TORRES ET. AL. J. CHEMOTHERAPY. 2011, 23, 87-91 |
| ENTEROCOCCUS FAECIUM_parC_F | 5'-TTCCCGTGCATTTCGATCAGTACTTC-3' | TORRES ET. AL. J. CHEMOTHERAPY. 2011, 23, 87-91 |

FIG. 15A

| FIG. 15 | FIG. 15A |
|---|---|
|  | FIG. 15B |

| | | |
|---|---|---|
| ENTEROCOCCUS FAECIUM_parC_R | 5'-CGTATGACAAAGGATTCGGTAAATC-3' | TORRES ET. AL. J. CHEMOTHERAPY. 2011, 23, 87-91 |
| SAUREUS_gyrA_F | 5'-GGATTAAATGAACAAGGTATGACACCG-3' | HIRAMATSU ET. AL. INT. J. ANTIMICROB. AGENTS 2012, 39, 478-485 |
| SAUREUS_gyrA_R | 5'-TAGTCATACGCGCTTCAGTATAACG-3' | HIRAMATSU ET. AL. INT. J. ANTIMICROB. AGENTS 2012, 39, 478-485 |
| SAUREUS_parC_F | 5'-TTAGGTGATCGCTTTGGAAGATATAG-3' | HIRAMATSU ET. AL. INT. J. ANTIMICROB. AGENTS 2012, 39, 478-485 |
| SAUREUS_parC_R | 5'-TACCATTGGTTCGAGTGTCG-3' | HIRAMATSU ET. AL. INT. J. ANTIMICROB. AGENTS 2012, 39, 478-485 |
| E COLI S83L SENSE | 5'-AATACCATCCCCATGGTGACTTGGCGGTCTATG-3' | AGILENT QUIKCHANGE PRIMER DESIGN |
| E COLI S83L ANTISENSE | 5'-CATAGACCGCCAAGTCACCATGGGGATGGTATT-3' | AGILENT QUIKCHANGE PRIMER DESIGN |
| E COLI S83R SENSE | 5'-CATCCCCATGGTGACAGGGGCGGTCTATGACAC-3' | AGILENT QUIKCHANGE PRIMER DESIGN |
| E COLI S83R ANTISENSE | 5'-GTGTCATAGACCGCCCCTGTCACCATGGGGATG-3' | AGILENT QUIKCHANGE PRIMER DESIGN |

FIG. 15B

COMPOUNDS FOR TREATMENT OF FLUOROQUINOLONE-RESISTANT BACTERIA

RELATED APPLICATIONS

This application is a National Stage filing under 35 U.S.C. § 371 of International Application No. PCT/US2015/021104, filed Mar. 18, 2015, which claims priority under 35 U.S.C. § 119(e) to U.S. Provisional Patent Application No. 61/954,141, filed Mar. 17, 2014, which applications are incorporated herein by reference.

GOVERNMENT SUPPORT

This invention was made with government support under Grant No. R01HL090699 awarded by the National Institutes of Health. The government has certain rights in the invention.

BACKGROUND OF THE INVENTION

Fluoroquinolones (FQs) are life-saving drugs and the most widely prescribed antibiotics to adults in the United States. Unfortunately, it is now well-established that bacterial resistance to FQs is significant, and resistance has been established to the point that these drugs are no longer useful for some of the most serious infections. For example, methicillin-resistant *Staphylococcus aureus* (MRSA) and vancomycin-resistant enterococci (VRE) harbor a key mutation in their DNA gyrase that render them insensitive to FQs. This mutation of a serine in the GyrA subunit near the enzyme active site is observed in close to 100% of MRSA and VRE. Thus there is a critical need for the discovery and development of novel compounds that are active against pathogenic bacteria, including bacteria possessing fluoroquinolone resistance (FQR). This need is already acute for MRSA and VRE, and will also become urgent for other pathogens as FQ-resistance continues to rise.

SUMMARY

Fluoroquinolones are one of the most commonly prescribed classes of antibiotics, but fluoroquinolone resistance (FQR) is widespread and increasing. Deoxynybomycin (DNM) is a natural product antibiotic with an unusual mechanism of action, inhibiting the mutant DNA gyrase that confers FQR. Unfortunately, isolation of DNM is difficult, and DNM is insoluble in aqueous solutions, making it a poor candidate for development. Here we describe a facile chemical route to produce DNM and derivatives. These compounds possess excellent activity against FQR methicillin-resistant *S. aureus* and vancomycin-resistant Enterococci clinical isolates and inhibit mutant DNA gyrase in vitro. Bacteria that develop resistance to DNM are re-sensitized to fluoroquinolones, indicating that resistance that emerges to DNM is treatable by the administration of fluoroquinolones or other antibiotics. Utilizing a DNM derivative, the first in vivo efficacy of the nybomycin class is demonstrated herein. The data therefore show that DNM derivatives can be used for the treatment of FQR infections.

Accordingly, the invention provides a compound of Formula I:

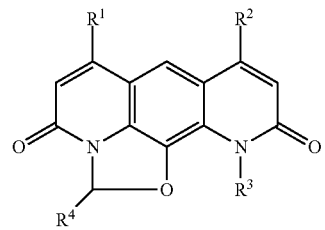

wherein
R$^1$ is (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched;
R$^2$ is (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched;
R$^3$ is (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched; and
R$^4$ is H, (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched;
provided that when R$^4$ is H, R$^1$, R$^2$, and R$^3$ are not each methyl.

A specific value for R$^1$ is methyl. Another specific value for R$^1$ is ethyl. Another specific value for R$^1$ is propyl.

A specific value for R$^2$ is methyl. Another specific value for R$^2$ is ethyl. Another specific value for R$^2$ is propyl.

A specific value for R$^3$ is methyl. Another specific value for R$^3$ is ethyl. Another specific value for R$^3$ is propyl. Another specific value for R$^3$ is butyl. Another specific value for R$^3$ is iso-butyl. Another specific value for R$^3$ is pentyl. Another specific value for R$^3$ is neo-pentyl. Another specific value for R$^3$ is hexyl.

A specific value for R$^4$ is H. Another specific value for R$^4$ is methyl. Another specific value for R$^4$ is ethyl.

In one embodiment, R$^1$ is methyl or ethyl; R$^2$ is methyl, ethyl, or propyl; R$^3$ is methyl, ethyl, propyl, or butyl; and R$^4$ is H or methyl.

In some embodiments, at least one of R$^1$-R$^3$ is methyl. In another embodiment, at least one of R$^1$-R$^3$ is not methyl. In some embodiments, at least one of R$^1$-R$^3$ is ethyl. In another embodiment, at least one of R$^1$-R$^3$ is not ethyl. In some embodiments, at least two of R$^1$-R$^3$ are methyl. In another embodiment, at least two of R$^1$-R$^3$ are not methyl.

In some embodiments, the compounds of Formula I have a solubility in pH 7.4 PBS of greater than about 15 µM, greater than about 20 µM, greater than about 40 µM, greater than about 50 µM, or greater than about 100 µM. In various embodiments, the compounds of Formula I have a solubility in DMSO of greater than about 1 mM, greater than about 1 mM, greater than about 3 mM, greater than about 4 mM, greater than about 5 mM, greater than about 10 mM, greater than about 20 mM.

In some embodiments, the compound is active against fluoroquinolone resistant bacteria with an MIC of less than 16 µg mL$^{-1}$, or less than 4 µg mL$^{-1}$. In other embodiments, the compound is active against fluoroquinolone resistant bacteria with an MIC of less than 0.3 µg mL$^{-1}$. In some embodiments, the compound is active against fluoroquinolone resistant bacteria with an MIC of less than 0.2 µg mL$^{-1}$.

In one embodiment, the compound is a compound selected from compounds 2-15:

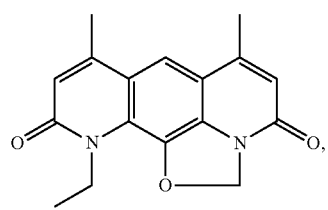
DNM-2
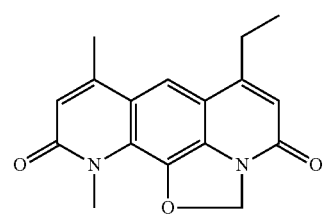
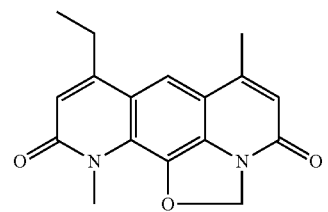
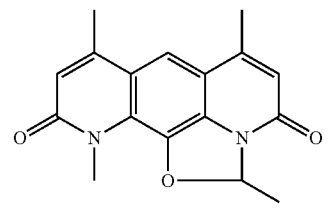
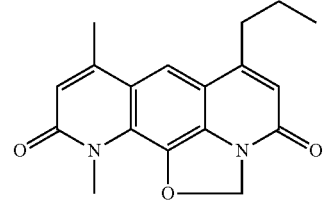
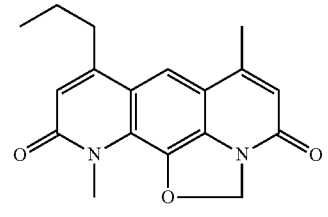
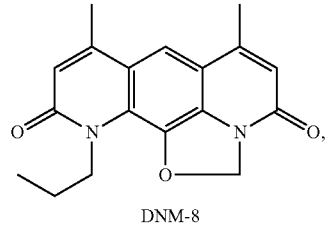
DNM-8
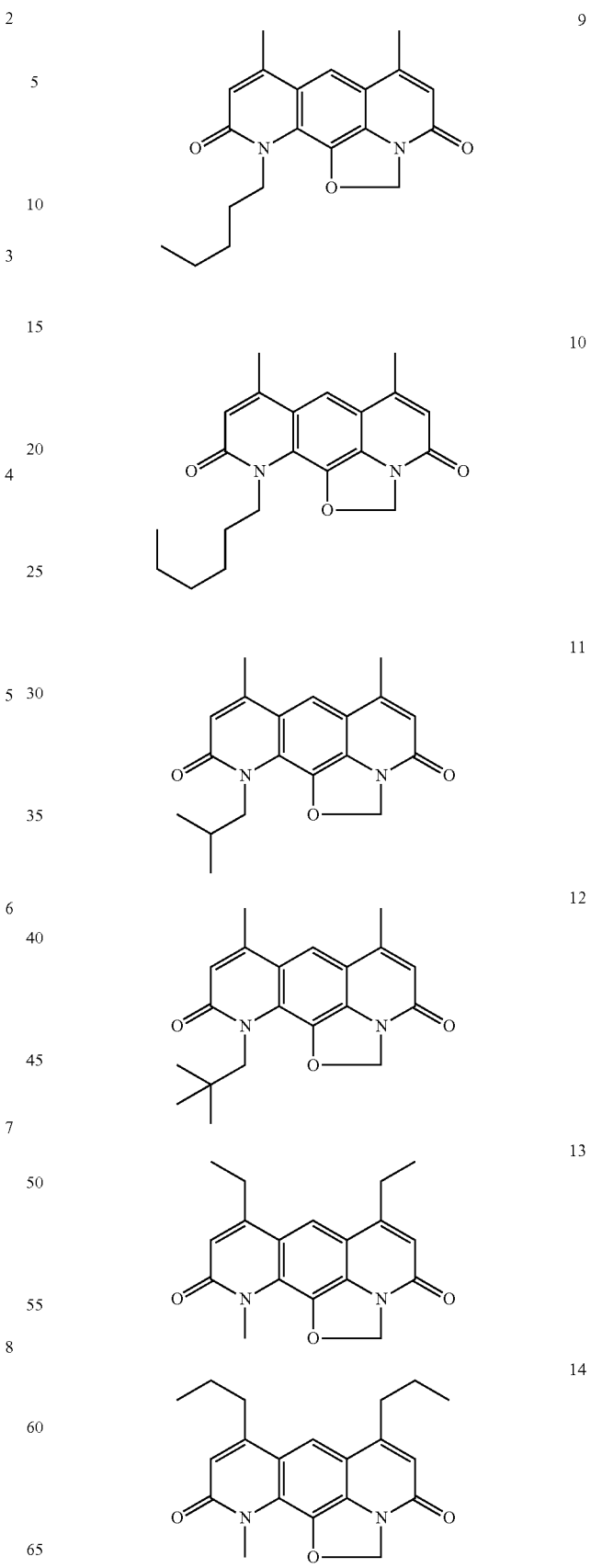

-continued

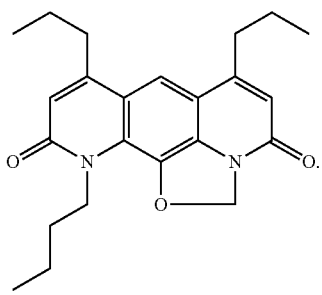

In one specific embodiment, the compound is one of compounds 2-6 and 8-9.

The invention also provides a pharmaceutical composition that includes a compound described herein, in combination with a pharmaceutically acceptable diluent, excipient, or carrier.

The invention further provides a method of killing or inhibiting the growth of a bacteria comprising contacting a bacteria with an effective antibacterial amount of a compound of Formula I. In some embodiments, the bacteria can be a methicillin-resistant *Staphylococcus aureus* (MRSA) or vancomycin-resistant enterococci (VRE).

The invention yet further provides a method of treating a bacterial infection in a subject comprising administering to a subject having a bacterial infection an effective amount of a compound of Formula I.

The invention also provides a method of treating an infection caused by fluoroquinolone-resistant bacteria comprising administering to a mammal in need of such treatment an effective antibacterial amount of a compound of Formula II:

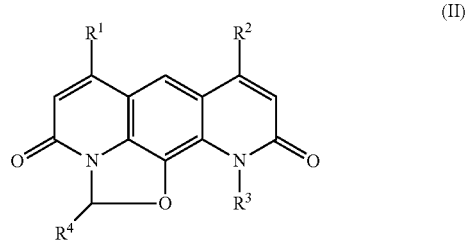

(II)

wherein
R$^1$ is (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched;
R$^2$ is (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched;
R$^3$ is (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched; and
R$^4$ is H, (C$_1$-C$_{12}$)alkyl, (C$_1$-C$_{12}$)alkyl(C$_3$-C$_{12}$)cycloalkyl, or (C$_3$-C$_{12}$)cycloalkyl, where alkyl can be straight or branched;
in combination with the administration of an effective antibacterial amount of a fluoroquinolone antibiotic, thereby killing or inhibiting the growth of the fluoroquinolone-resistant bacteria and treating the infection. The fluoroquinolone antibiotic can be, for example, ciprofloxacin, levofloxacin, moxifloxacin, trovafloxacin, or DW286. The administration can be concurrent, such as in the same pharmaceutical formulation, or the administration can be separate and concurrent.

Variations of R$^1$-R$^4$ can be as described above for Formula I. In some embodiments, the compound of Formula II can be a compound of Formula I.

In some embodiments, the fluoroquinolone-resistant bacteria are gram positive bacteria. In further embodiments, an infection is caused methicillin-resistant *Staphylococcus aureus* (MRSA) or vancomycin-resistant enterococci (VRE). In yet further embodiments, the bacteria being killed or inhibited from growing is *Staphylococcus aureus, Staphylococcus epidermidis, Staphylococcus haemolyticus, Streptococcus pneumonia, Clostridium difficile, E. faecium*, or *E. faecium*.

The invention provides novel compounds as described herein, intermediates for the synthesis of compounds described herein, as well as methods of preparing compounds of described herein. The invention also provides compounds as described herein that are useful as intermediates for the synthesis of other useful compounds. The invention provides for the use of compounds described herein for killing gram positive bacteria, or for the manufacture of medicaments useful for the treatment of bacterial infections in a mammal, such as a human. Useful pharmaceutical formulations of the compound or a corresponding medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 15. Primers used for sequencing and for site directed mutagenesis (Table 7).

DETAILED DESCRIPTION

Figure 1:
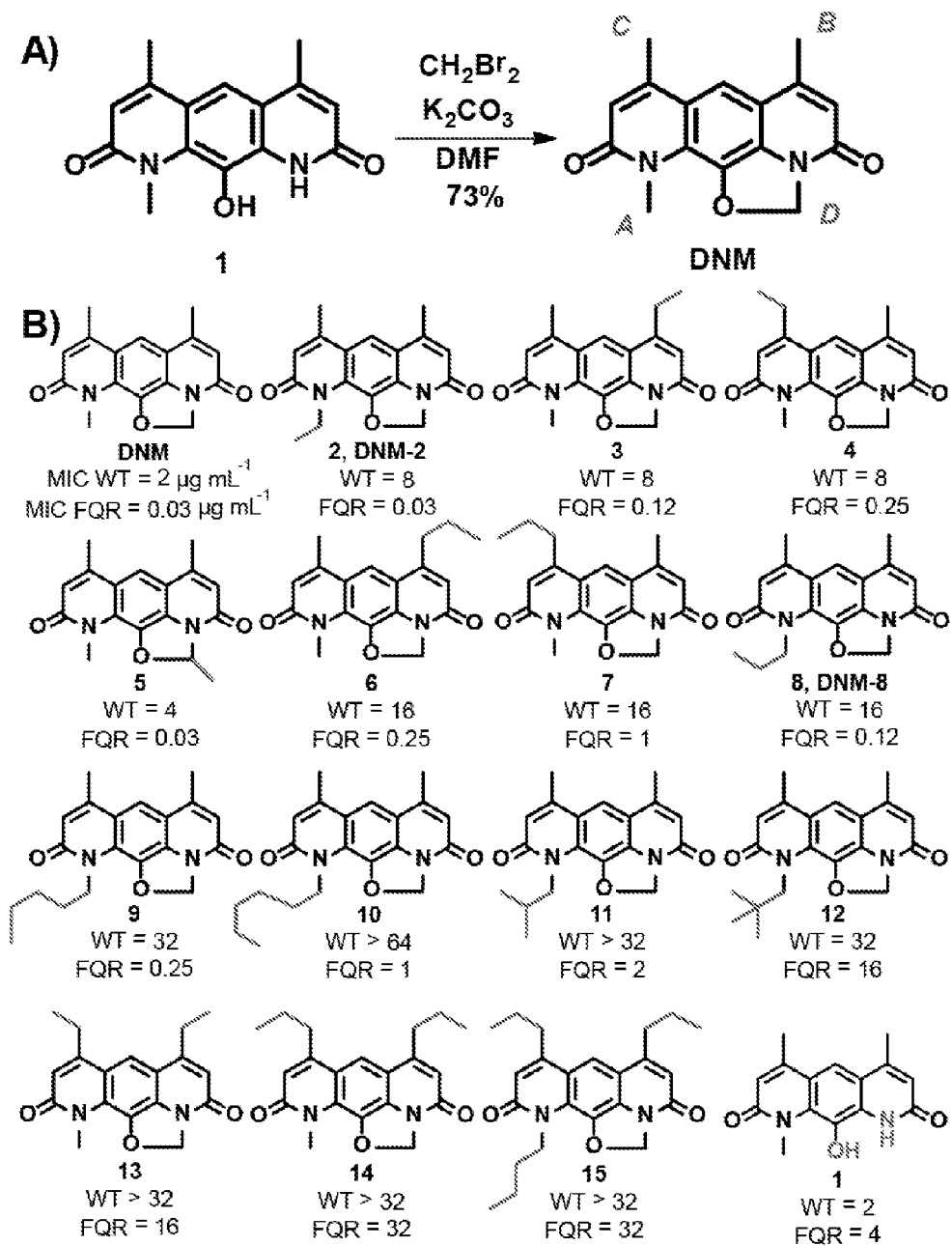
FIG. 1. Synthesis and antibacterial activity of DNM and derivatives. (A) Final step in the synthesis of DNM. The letters A, B, C, and D around the structure of DNM denote sites of derivitization. (B) Structure of DNM and derivatives and their activities against wild type *S. aureus* (29213, WT) and fluoroquinolone resistant *S. aureus* (NRS3, FQR). Activity is from three independent replicates of the microdilution broth assay and is reported as the MIC in µg mL$^{-1}$. (C) Dose response curves for FQ sensitive *S. aureus* (29213) and FQR *S. aureus* (NRS3) treated with DNM. Data shown is from three independent replicates±the standard error (SEM). (D) Dose response curves for FQ sensitive *Enterococcus* (29212) and FQR *Enterococcus* (S235) treated with DNM. Data shown is from three independent replicates±SEM.
Figure 1:
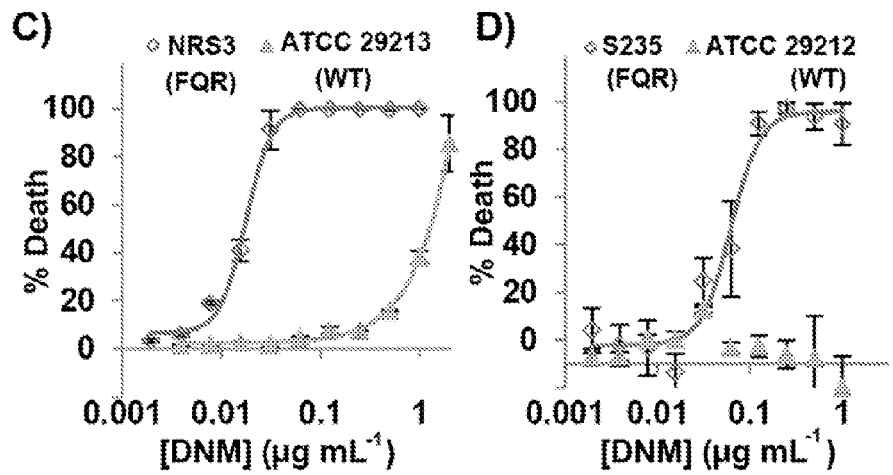

Fluoroquinolones (FQs) were introduced into the clinic in the early 1980s and since then have become one of the most widely prescribed classes of antibiotics[1-3]. While early FQs were primarily used to treat Gram-negative infections, later generation FQs are also commonly employed against infections caused by Gram-positive pathogens[1,4]. FQs are prescribed for severe or antibiotic-resistant urinary tract infections, respiratory tract infections[2,4], gonoccocal infections, tuberculosis, and as a prophylactic for anthrax[5]. FQs act by inhibiting bacterial type IIA topoisomerases, specifically DNA gyrase (composed of GyrA and B subunits) and topoisomerase IV (composed of ParC and E subunits). These enzymes catalyze the introduction of negative supercoils and the decatenation of interlinked chromosomes, respectively[6-8].

While FQs have demonstrated great utility in the clinic, their widespread use has resulted in significant resistance[4]. Nearly all vancomycin-resistant enterococcus (VRE) and methicillin-resistant S. aureus (MRSA) are also resistant to FQs[9], thus FQs can no longer be used to treat such infections. FQs are commonly prescribed for N. gonorrhoeae and P. aeruginosa infections, but FQR is now observed in a substantial fraction of these isolates, necessitating other treatments[10]. Target site mutation is the major contributor to FQR[1,4], with high-level resistance observed in bacteria possessing key mutations in both GyrA and ParC[4]. VRE and MRSA both harbor these target site mutations, with point mutations in the quinolone resistance-determining region (QRDR) of the GyrA subunit of DNA gyrase and the ParC subunit of topoisomerase IV. These mutations alter residues important for the binding of FQs resulting in an approximately 10-fold decrease in binding affinity[11-12]. Nearly 100% of MRSA substitute Ser84 of GyrA with Leu[13-21]. Similarly, nearly all FQR VRE substitute Ser83 of GyrA with Ile, Arg or Tyr[22-26].

Nybomycin (NM) is a natural product first identified from a culture of a streptomycete isolated from a Missouri soil sample and found to have antibacterial activity[27-28]. During efforts to determine its structure, Rinehart and coworkers synthesized a related compound, deoxynybomycin (DNM, FIG. 1A), which was later found also to be a natural product and to have more potent activity than NM against a range of bacteria[29-30]. More recently, DNM was found to have activity against FQR MRSA with the S84L mutation in GyrA of DNA gyrase[15]. However, isolation of NM and DNM from natural sources is non-trivial[31], and the only reported total synthesis of DNM is very low yielding[32-33]. Additionally, the low solubility of DNM in any solvent other than concentrated acid presents challenges for its biological evaluation and limits its potential in vivo.

Described herein is an efficient total synthesis of DNM, and modifications of this route are used to construct the first DNM derivatives. DNM and several of the derivatives show outstanding antibacterial potency and selectivity against FQR MRSA and VRE clinical isolates. DNM and derivatives inhibit the mutant DNA gyrase responsible for FQR, and resistance to DNM and derivatives results in re-sensitization to FQs suggesting a resistance cycling that could be useful in the clinic. Finally, utilizing a DNM derivative with superior solubility and pharmacokinetic properties, the first in vivo activity of this class of compounds is demonstrated.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "alkyl" refers to a straight- or branched-chain alkyl group having from 1 to about 20 carbon atoms in the chain. For example, the alkyl group can be a $(C_1-C_{20})$alkyl, a $(C_1-C_{12})$alkyl, $(C_1-C_8)$alkyl, $(C_1-C_6)$alkyl, or $(C_1-C_4)$ alkyl. Examples of alkyl groups include methyl (Me), ethyl (Et), n-propyl, isopropyl, butyl, isobutyl, sec-butyl, tert-butyl (t-Bu), pentyl, isopentyl, neo-pentyl (—CH$_2$-tert-butyl), hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group. In some embodiments, alkyl groups can be substituted with hydroxy, halo, trifluoromethyl, or trifluoromethoxy. In some embodiments, shorter alkyls (e.g., $C_1$, $C_2$ or $C_3$ can be omitted from the definition of a particular alkyl group.

The term "cycloalkyl" refers to a saturated or partially saturated, monocyclic, fused polycyclic, or spiro polycyclic carbocycle having from 3 to 12 ring atoms per carbocycle, and can be optionally substituted or unsubstituted. In some embodiments, an alkyl group refers to a cycloalkyl group that accordingly includes a ring structure. Such alkyl groups include (cycloalkyl)-alkyl groups. Illustrative examples of cycloalkyl groups include cyclopropyl, cyclobutyl, cyclopentyl, cyclohexyl, cycloheptyl, cyclooctyl, cyclononyl, and cyclodecyl, where the cycloalkyl group is attached at the location of any hydrogen atom of the parent cycloalkane.

The term "$(C_1-C_{12})$alkyl$(C_3-C_{12})$cycloalkyl" thus refers to a cycloalkyl group that has one or more alkyl substituents on the ring of the cycloalkyl. Typical $(C_1-C_{12})$alkyl$(C_3-C_{12})$ cycloalkyl groups include methylcyclopropyl, ethylcyclopropyl, methylcyclobuyl, ethylcyclobuyl, methylcyclopentyl, ethylcyclopentyl, methylcyclohexyl, and ethylcyclohexyl, where the alkyl group is attached at any available carbon of the cycloalkane ring.

"Halo" refers to a halogen substituent such as fluoro, chloro, bromo, or iodo.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Methods of Making the Compounds of the Invention

The invention also relates to methods of making the compounds and compositions of the invention. The compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure, 5$^{th}$ Ed.* By M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis*, Second Edition, Cary and Sundberg (1983); *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Suitable solvents can include DMF, DMA, DME, DMSO, methylene chloride, chloroform, alkanes, aryls, alcoholic solvents such as methanol or ethanol, or water, or combinations thereof, depending on the solubility of the reactants and reagents.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group. The particular removable blocking group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The R groups of Formula (I) can also be protecting groups, as described herein.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art. For further detail regarding carboxylic acid protecting groups and other protecting groups for acids, see Greene, cited above. Such groups include by way of example and not limitation, esters, amides, hydrazides, and the like.

Useful synthetic techniques and methods are also described by U.S. Publication No. 2015/0011509 (Hergenrother et al.) and PCT Publication No. WO 2014/168991 (Hergenrother et al.), which techniques and methods are incorporated herein by reference.

Total Synthesis of DNM and Construction of Derivatives.

Due to the documented difficulty of isolating DNM from natural sources[31], we aimed to develop an efficient, modular, and flexible synthesis of DNM that could also be used to construct derivatives. Previously, we reported a synthesis of the natural product deoxynyboquinone (DNQ) that relies on a mixed Suzuki cross coupling followed by a palladium-catalyzed ring closing and deprotection to give diazaanthracenol (1, FIG. 1A)[34]. To construct DNQ, 1 is oxidized to give the desired quinone[34]. We found that 1 could be converted to DNM in a single step by insertion of the methylene bridge in a reaction inspired by Rinehart's degradation studies and by bridge insertions in similar systems[32-33,35]. Reaction of 1 with dibromomethane gave DNM in a 73% yield (FIG. 1A). Through this route, DNM was obtained in 7 steps with an overall yield of 11%, an improvement over the only other reported total synthesis (0.84% overall yield)[32-33].

This flexible synthetic route also allowed for rapid generation of a variety of derivatives that have not been found as natural products. We hypothesized that addition of alkyl chains would disrupt π-stacking between DNM molecules, thus increasing both aqueous and organic solubility, similar to what was observed with DNQ derivatives[36]. By changing the iodoamides used in the Suzuki cross coupling (see General protocol A in the Materials and Methods section of Example 2), three compounds were synthesized that substituted ethyl for methyl at positions A, B, and C (compounds 2, 3, and 4 respectively, FIG. 1B). The derivative with a methyl substitution at D was generated by using 1,1-dibromoethane in place of dibromomethane in the final step to provide compound 5 (FIG. 1B). Other compounds with single sites of derivatization (6-12) and multiple sites of derivatization (13-15) were also constructed. Full synthetic routes along with experimental details and characterization data can be found in the Materials and Methods section of Example 2. Compounds with small alkyl appendages have markedly improved solubility (3 to 23 fold) in pH 7.4 phosphate buffered saline relative to DNM (Table 1), and all compounds synthesized also have improved DMSO solubility compared to the parent compound (Table 1).

TABLE 1

Solubility and Activity of DNM and its derivatives.

| CIP | DAPT | VANC | LINEZ | DNM | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|---|
| Solubility in pH 7.4 PBS (μM) | | | | | | | | | | | | | | | | | | |
|  |  |  |  | 9 ± 3 | 121 ± 4 | 27 ± 1 | 53 ± 8 | ND | ND | ND | 68 ± 9 | ND | ND | ND | ND | 48 ± 8 | <1 | ND |
| Solubility in DMSO (mM) | | | | | | | | | | | | | | | | | | |
|  |  |  |  | 0.2 | 4 | 1.3 | 4.7 | 3.4 | 6.4 | 5.8 | 11.3 | 26.9 | 56.7 | 7.1 | 38.7 | 5.2 | 18.3 | 4.2 |
| MIC against *S. aureus* 29213 (μg mL$^{-1}$) WT GyrA and WT ParC | | | | | | | | | | | | | | | | | | |
| 0.25-0.5 | 2 | 1 | 2 | >1 | 8 | 8 | 8 | 4 | 16 | 16 | 16 | 32 | >64 | >32 | 32 | >32 | >32 | >32 |
| MIC against *S. aureus* NRS3 (μg mL$^{-1}$) S84L GyrA and S80F ParC | | | | | | | | | | | | | | | | | | |
| >64 | 8 | 8 | 0.5 | 0.03 | 0.03 | 0.12 | 0.25 | 0.03 | 0.25 | 1 | 0.12 | 0.25 | 1 | 2 | 16 | 16 | 32 | 32 |

The solubility in PBS (pH 7.4) was determined by weighing a small amount of compound (0.5-2.0 mg) into a 1.7 mL Eppendorf tube. Enough PBS was added to make a 1 mg/mL solution. Compounds were then assessed by LC-MS and compared to a calibration curve to determine the solubility. Additional details are found in the Examples section below. Data shown is from three independent replicates±SEM. ND=not determined DMSO solubility of compounds was determined by weighing a small amount of compound (typically 1-2 mg) into a glass vial and adding DMSO dropwise until the compound was fully dissolved. Between DMSO additions, the vial was vortexed and sonicated. MICs with ciprofloxacin (CIP), daptomycin (DAPT), vancomycin (VANC), linezolid (LINEZ), deoxynybomycin (DNM), and DNM derivatives were determined using the microdilution broth method as outlined by the Clinical and Laboratory Standards Institute.

Evaluation of DNM and Derivatives Against FQR MRSA and VRE.

DNM was evaluated against both FQ sensitive *S. aureus* (ATCC 29213) and FQR MRSA (NRS3 which has GyrA S84L and ParC S80F). DNM showed modest activity against the FQ-sensitive (FQS) strain 29213. However, DNM showed excellent activity against the FQR NRS3 (MIC=0.03 μg mL$^{-1}$, FIGS. 1B and 1C). This MIC compares favorably with standard of care treatments for Gram-positive infections including vancomycin (MIC for NRS3=8 μg mL$^{-1}$), daptomycin (MIC for NRS3=8 μg mL$^{-1}$) and linezolid (MIC for NRS3=0.5 μg mL$^{-1}$). The sensitivity of FQR VRE was also explored. DNM had no detectable activity against FQ sensitive *Enterococcus* (ATCC 29212, MIC>1.0 μg mL$^{-1}$), but it potently inhibited the growth of FQR VRE (clinical isolate 5235 which has GyrA S83I and ParC S80I, MIC=0.125 μg mL$^{-1}$, FIG. 1D). DNM was also evaluated against a panel of Gram-negative bacteria (Table 2). It showed no detectable activity against wild type or FQR *P. aeruginosa* or *A. baummannii*. Moderate activity was seen with a DNM derivative against a permeabilized strain of *E. coli*, suggesting that DNM and its derivatives are unable to penetrate Gram-negative bacteria.

The ciprofloxacin (CIP) sensitivity where a strain was considered sensitive (S) or resistant (R) based on the CLSI guidelines for each bacteria. MICs with CIP, DNM, DNM-2, and DNM-8 were determined using the microdilution broth method as outlined by the Clinical and Laboratory Standards Institute. *E. coli* MG1655 and the ΔAcrB strain were obtained from Prof. Cari Vanderpool at UIUC. *P. aeruginosa* clinical isolates were obtained from Cubist Pharmaceuticals (Lexington, Mass.) (Williams et al., *FEMS Microbiol Lett* 322, 41-50, (2011)). *A. baumannii* clinical isolates were obtained from Dr. John Quale at the Division of Infectious Diseases at SUNY Downstate Medical Center (Bratu et al., *Antimicrob Agents Chemother* 52, 2999-3005, (2008)). ND=not determined *These strains were previously determined to be CIP resistant.

DNM derivatives were evaluated against both FQ sensitive *S. aureus* (ATCC 29213) and FQR MRSA (NRS3), and their MIC values are listed in FIG. 1B. Similar to DNM, most derivatives showed significantly enhanced activity against FQR NRS3 compared to FQS 29213. In general, compounds with a single methyl addition (2-5) retained good activity against NRS3. Further substitution at position B was relatively well tolerated (6), while substitution at position C was generally less well tolerated (7). Compounds possessing longer chains at position A generally retained potency (8-10). However, compounds with bulky substitutions at position A (11-12), multiple substitutions (13-15), or without the methylene bridge (1) were markedly less active.

Figure 2:
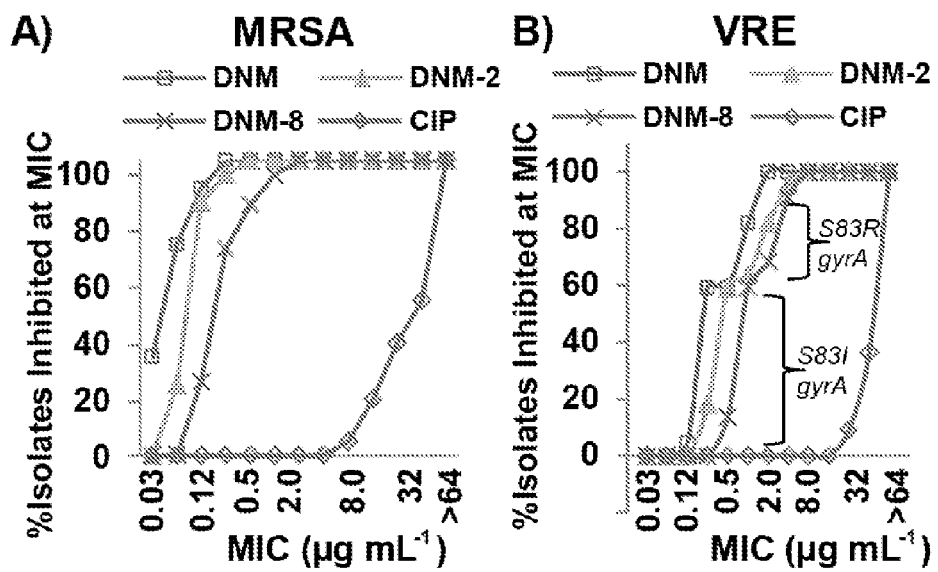
FIG. 2. Sensitivity of MRSA and VRE clinical isolates to DNM, DNM-2, DNM-8, and ciprofloxacin (CIP). (A) The percentage of MRSA clinical isolates (n=21) with an MIC at or lower than the concentration shown. (B) The percentage of VRE clinical isolates (n=22) with an MIC at or lower than the concentration shown.

Activity of DNM or derivatives against FQR clinical isolates. DNM and two of the most potent derivatives (DNM-2 and DNM-8) were evaluated against a panel of MRSA and VRE clinical isolates (FIGS. 2A and 2B). As shown in FIG. 2, all MRSA and VRE strains were sensitive to these compounds and resistant to ciprofloxacin (CIP). In order to understand this selectivity, the QRDRs of GyrA and ParC for many of these isolates were sequenced (Table 3 and Table 4).

TABLE 2

Activity of DNM and its derivatives against Gram-negative bacteria.

| Strain | CIP (S/R) | CIP MIC (μg mL$^{-1}$) | DNM MIC (μg mL$^{-1}$) | DNM-2 MIC (μg mL$^{-1}$) | DNM-8 MIC (μg mL$^{-1}$) | gyrA mutation | parC mutation |
|---|---|---|---|---|---|---|---|
| *E. coli* ATCC 25922 | S | 0.025 | >4 | >24 | >32 | none | none |
| *E. coli* MG1655 | S | 0.025 | ND | >24 | ND | none | none |
| *E. coli* MG1655 ΔAcrB | S | 0.008 | ND | 2 | ND | none | none |
| *P. aeruginosa* PAO1 | S | 0.5 | >4 | >24 | >32 | none | none |
| PA1000 | R* | ND | >4 | >24 | >32 | ND | ND |
| PA1586 | R* | ND | >4 | >24 | >32 | ND | ND |
| *A. baumannii* ATCC 19606 | S | 1 | >4 | >24 | >32 | none | none |
| *A. baumannii* KB349 | R* | >32* | >4 | >24 | >32 | S83L | none |
| *A. baumannii* KB304 | R* | 24* | >4 | >24 | >32 | S83L | none |

TABLE 3

Sensitivity of MRSA clinical isolates to CIP, DNM, DNM derivatives, and other antibiotics and tabulated data from FIG. 2A.

| Strain ID | CIP S/I/R | CIP MIC (μg mL$^{-1}$) | DNM MIC (μg mL$^{-1}$) | DNM-2 MIC (μg mL$^{-1}$) | DNM-8 MIC (μg mL$^{-1}$) | Vanc MIC (μg mL$^{-1}$) | Amp MIC (μg mL$^{-1}$) | Novo MIC (μg mL$^{-1}$) | gyrA mutations | parC mutations |
|---|---|---|---|---|---|---|---|---|---|---|
| SAU.42 | S | 0.25 | 1 | 2 | 8 | 1 | 2 | 0.5 | ND | ND |
| SAU.1118 | S | 0.5 | 1 | 2 | 8 | 2 | >64 | 0.5 | ND | ND |
| SAU.3017 | S | 1 | 1 | 4 | 4 | 1 | >64 | 0.5 | ND | ND |
| SAU.3021 | R | 8 | 0.031 | 0.063 | 0.125 | 1 | >64 | 0.25 | ND | ND |
| SAU.446 | R | 16 | 0.25 | 0.125 | 0.25 | 2 | >64 | 0.5 | ND | ND |
| SAU.491 | R | 16 | 0.125 | 0.125 | 0.5 | 2 | >64 | 0.5 | Ser84Leu | Ser80Phe |
| SAU.555 | R | 16 | 0.125 | 0.25 | 0.5 | 1 | >64 | 0.25 | ND | ND |
| SAU.493 | R | 32 | 0.063 | 0.125 | 0.25 | 1 | >64 | 0.5 | Ser84Leu | Ser80Phe |
| SAU.710 | R | 32 | 0.031 | 0.063 | 0.125 | 2 | >64 | 0.5 | Ser84Leu | Ser80Phe |
| SAU.3024 | R | 32 | 0.031 | 0.125 | 0.125 | 2 | >64 | 0.5 | ND | ND |
| SAU.3026 | R | 32 | 0.125 | 0.125 | 0.25 | 1 | >64 | 0.5 | ND | ND |
| SAU.419 | R | 64 | 0.125 | 0.063 | 0.25 | 4 | >64 | 0.25 | ND | ND |
| SAU.846 | R | 64 | 0.031 | 0.25 | 0.5 | 8 | >64 | 0.125 | ND | ND |
| SAU.2996 | R | 64 | 0.25 | 0.5 | 2 | 1 | >64 | 0.5 | ND | ND |
| SAU.447 | R | >64 | 0.063 | 0.125 | 1 | 2 | >64 | 0.25 | ND | ND |
| SAU.489 | R | >64 | 0.031 | 0.125 | 0.25 | 2 | >64 | 0.25 | Ser84Leu | Ser80Tyr |
| SAU.492 | R | >64 | 0.063 | 0.125 | ND | 1 | >64 | 0.5 | Ser84Leu | Ser80Tyr |
| SAU.494 | R | >64 | 0.063 | 0.125 | 0.25 | 1 | >64 | 0.125 | Ser84Leu | Ser80Phe |
| SAU.495 | R | >64 | 0.063 | 0.125 | 0.25 | 2 | >64 | 0.5 | Ser84Leu | Ser80Phe |
| SAU.496 | R | >64 | 0.063 | 0.125 | 0.25 | 1 | >64 | 0.5 | Ser84Leu | Ser80Phe |
| SAU.669 | R | >64 | 0.031 | 0.063 | 0.125 | 2 | >64 | 0.5 | ND | ND |
| SAU.708 | R | >64 | 0.063 | 0.125 | 1 | 2 | 64 | 0.25 | Ser84Leu | Ser80Phe Glu84Lys |
| SAU.709 | R | >64 | 0.063 | 0.125 | 0.25 | 1 | >64 | 0.5 | Ser84Leu | Ser80Tyr Glu84Gly |
| SAU.3025 | R | >64 | 0.031 | 0.063 | 0.125 | 1 | 64 | 0.25 | ND | ND |

For Table 3: The ciprofloxacin (CIP) sensitivity where a strain was considered sensitive (S) if it had an MIC≤4 μg mL$^{-1}$, intermediate (I) with a 16>MIC>4 μg mL$^{-1}$, or resistant (R) with a MIC≥16 μg mL$^{-1}$. MICs with CIP, DNM, DNM-2, DNM-8, Vancomycin (Vanc), Ampicillin (Amp), and Novobiocin (Novo) were determined using the microdilution broth method as outlined by the Clinical and Laboratory Standards Institute. QRDR mutations were determined as described in the text using primers (primer sequences can be found in Table 7 (see FIG. 15). Clinical isolates were obtained from Cubist Pharmaceuticals (Lexington, Mass.). ND=not determined CIP resistant strains are graphed in FIG. 2A.

TABLE 4

Sensitivity of ATCC strains and VRE clinical isolates to CIP, DNM, and DNM derivatives and tabulated data from FIG. 2B.

| Strain | Species | CIP (S/I/R) | Cipro MIC (μg mL$^{-1}$) | DNM MIC (μg mL$^{-1}$) | DNM-2 MIC (μg mL$^{-1}$) | DNM-8 MIC (μg mL$^{-1}$) | gyrA mutations | parC mutations |
|---|---|---|---|---|---|---|---|---|
| ATCC 29212 | E. faecalis | S | 0.5-2 | >1 | 8 | 8 | WT | WT |
| ATCC 19433 | E. faecalis | S | 2 | >1 | 8 | 16 | WT | WT |
| S235 | E. faecium | R | >64 | 0.125 | 0.5 | 1 | Ser83Ile | Ser80Ile |
| S51 | E. faecium | R | >64 | 0.25 | 0.5 | 1 | Ser83Ile | Ser80Ile |
| S122 | E. faecium | R | 64 | 0.25 | 0.5 | 1 | Ser83Ile | Ser80Ile |
| S226 | E. faecium | R | 64 | 0.25 | 0.5 | 1 | Ser83Ile | Ser80Ile |
| S344 | E. faecium | R | >64 | 0.25 | 0.5 | 1 | Ser83Ile | Ser80Ile |
| S234 | E. faecalis | R | 32 | 0.25 | 0.25 | 0.5 | Ser83Ile | Ser80Ile Glu84Asp |
| S557 | E. faecium | R | >64 | 0.25 | 0.25 | 0.5 | Ser83Ile | Ser80Ile |
| C27569 | E. faecium | R | >64 | 0.25 | 0.25 | 1 | Ser83Ile | Ser80Ile |
| C28535 | E. faecalis | R | 32 | 0.25 | 0.25 | 1 | Ser83Ile | Ser80Ile |
| D1 | E. faecium | R | >64 | 0.25 | 0.5 | 0.5 | Ser83Ile | Ser80Ile |
| C21667 | E. faecalis | R | >64 | 0.25 | 0.5 | 1 | Ser83Ile | Ser80Ile |
| C28036 | Ent. Spp. | R | 64 | 0.25 | 0.5 | 1 | Ser83Ile | Ser80Ile |
| SL152 | E. faecium | R | >64 | 0.25 | 0.5 | 1 | Ser83Ile | Ser80Ile |
| S206 | E. faecalis | R | 64 | 1 | 2 | 4 | Ser83Arg | Ser80Ile |
| U63 | E. faecium | R | >64 | 1 | 4 | 4 | Ser83Arg | Ser80Ile |
| U275 | E. faecium | R | >64 | 1 | 2 | 4 | Ser83Cys Glu87Gly | Ser80Ile |
| U464 | E. faecium | R | >64 | 1 | 2 | 2 | Ser83Arg | Ser80Ile |
| S34 | E. faecalis | R | 64 | 1 | 1 | 2 | Ser83Ile | Ser80Arg |
| C27282 | E. faecium | R | 64 | >1 | 4 | 8 | Ser83Arg | Ser80Arg |
| U503 | E. faecium | R | >64 | >1 | 4 | 4 | Ser83Arg | Ser80Ile |
| U563 | E. faecium | R | >64 | >1 | 2 | 4 | Ser83Arg | Ser80Ile |
| C21190 | E. faecium | R | >64 | >1 | 8 | 8 | Ser83Arg | Ser80Ile |

The ciprofloxacin (CIP) sensitivity where a strain was considered sensitive (S) if it had an MIC≤4 μg mL$^{-1}$, intermediate (I) with a 16>MIC>4 μg mL$^{-1}$, or resistant (R) with a MIC≥16 μg mL$^{-1}$. MICs with CIP, DNM, DNM-2, and DNM-8 were determined using the microdilution broth method as outlined by the Clinical and Laboratory Standards Institute CLSI. QRDR mutations were determined as described in the text using primers (primer sequences can be found in Table 7). CIP resistant strains are graphed in FIG. 2B.

While different substitution patterns were found for MRSA ParC, all sequenced strains have the same mutation in GyrA (S84L) consistent with the notion that this mutation sensitizes bacteria to DNM. Similar to the MRSA isolates, the VRE isolates have many different substitutions in ParC which do not appear to correlate with sensitivity. Unlike the MRSA isolates, the majority of VRE isolates have two different substitutions for GyrA (S83I or S83R). The sensitivity of these strains is affected by this substitution with VRE harboring the S83I mutation being very sensitive to DNM (MIC=0.125 to 1 μg mL$^{-1}$) and those with the S83R mutation being less sensitive (MIC≥1 μg mL$^{-1}$). The activity of the DNM-2 and DNM-8 against these panels of clinical isolates closely mirrors that of DNM (FIGS. 2A and B). Full details of the sensitivity of each strain can be found in Table 3 and Table 4.

Inhibition of Mutant DNA Gyrase by DNM and Derivatives.

Figure 5:
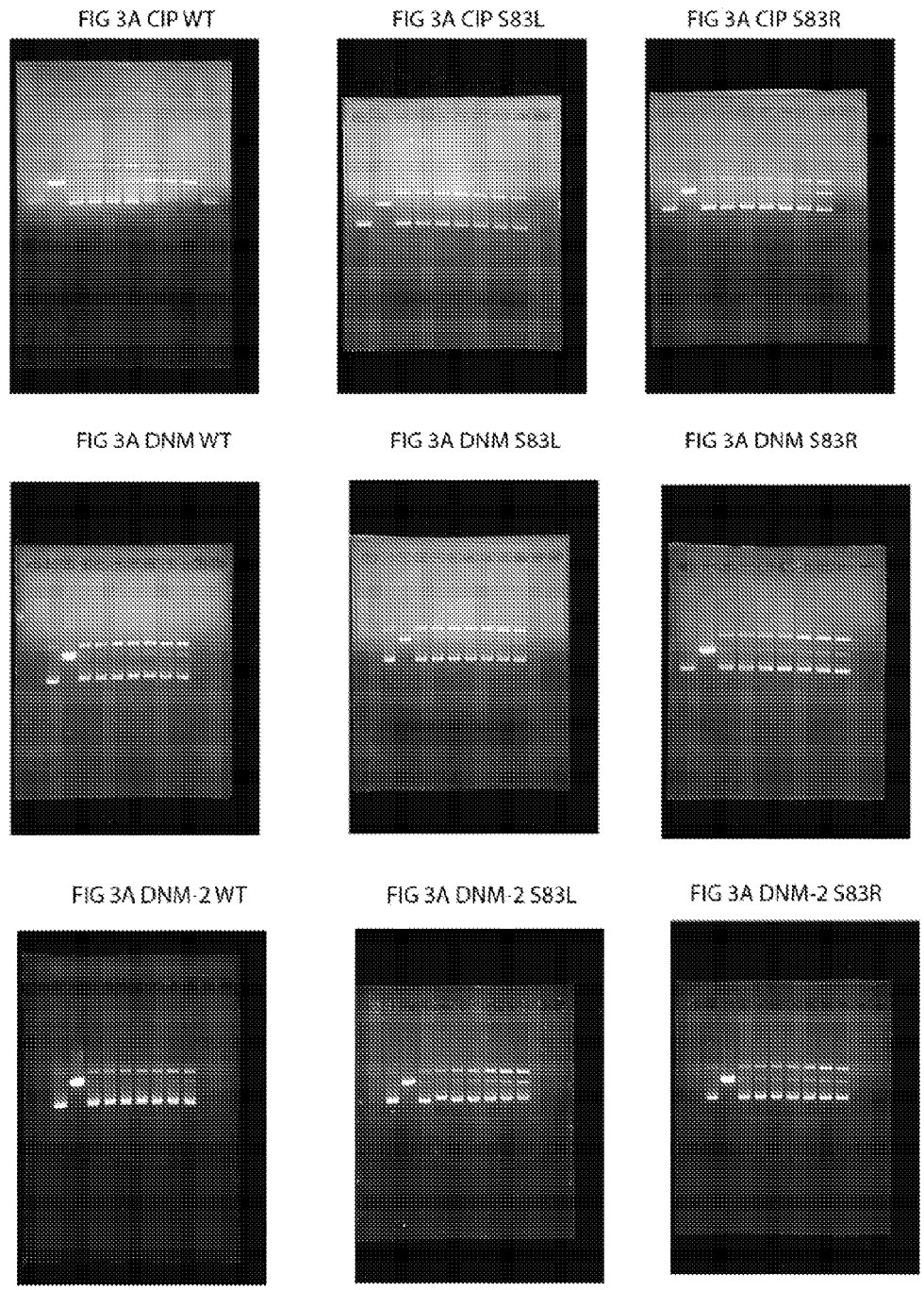
FIG. 5. Full gels from FIG. 3A.
Figure 6A:
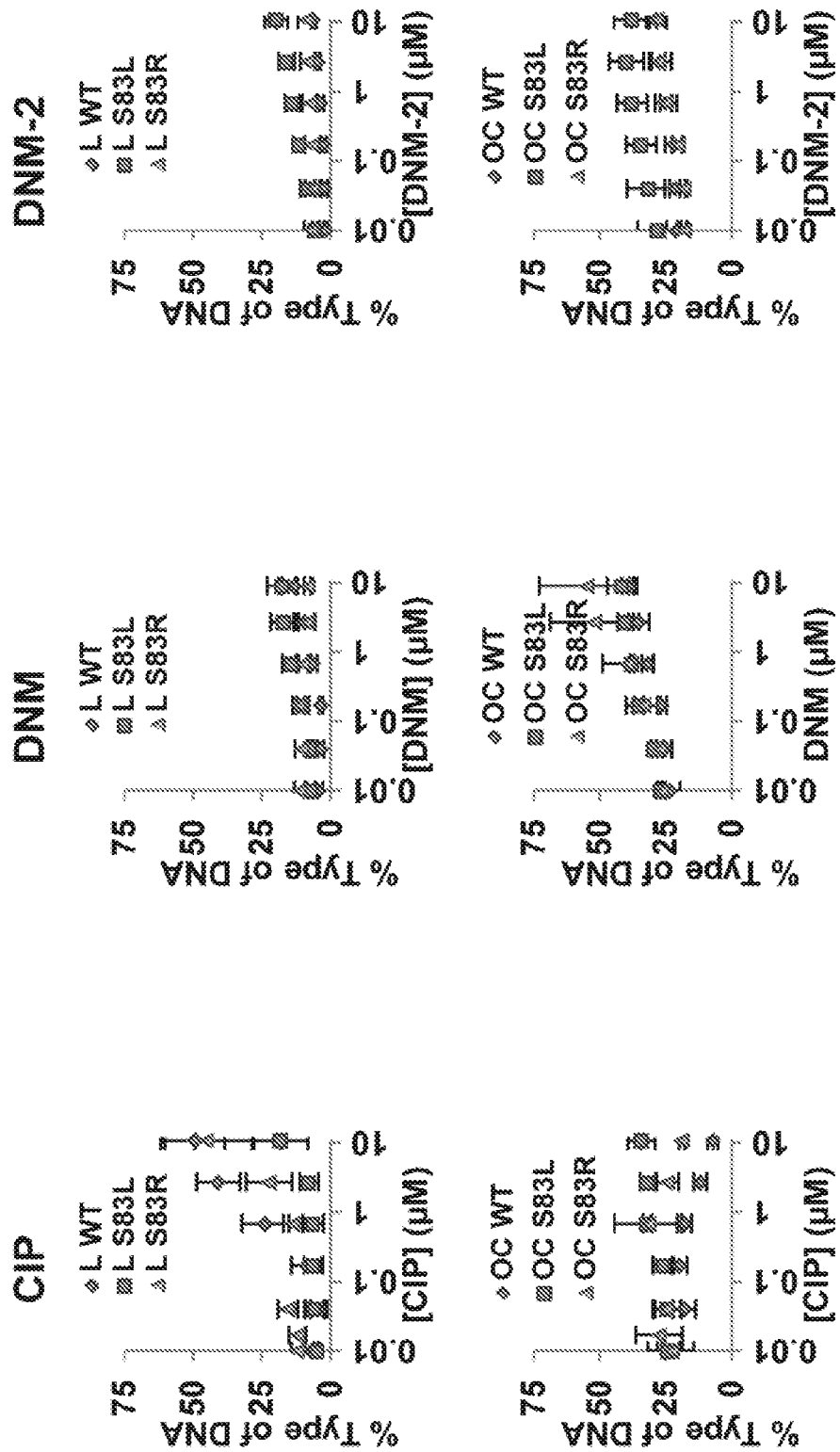
FIG. 6. Quantification of gels from FIG. 3 (Inhibition of wt and mutant DNA gyrase). (A) Quantification of DNA cleavage assay with WT, S83L, and S83R E. coli DNA gyrase in the presence of increasing concentrations of CIP, DNM, and DNM-2. Concentrations were 0.01, 0.04, 0.017, 0.68, 2.7, and 10.8 µM except for DNM which was 8.9 µM for the highest concentration. Top row is the quantification of the linear band and bottom row is quantification of the open circular (nicked) band. (B) Quantification of time course of DNA cleavage of 5 µM CIP, 1 µM DNM, and 1 µM DNM-2 with WT, S83L, and S83R DNA gyrase. Time points were 0, 1, 3, 5, 10, 15, 20, 30, 60, and 90 min. Top row is the quantification of the linear band and bottom row is quantification of the open circular (nicked) band. Data shown is from three independent replicates±SEM. Quantification was performed using ImageJ software.
Figure 6B:
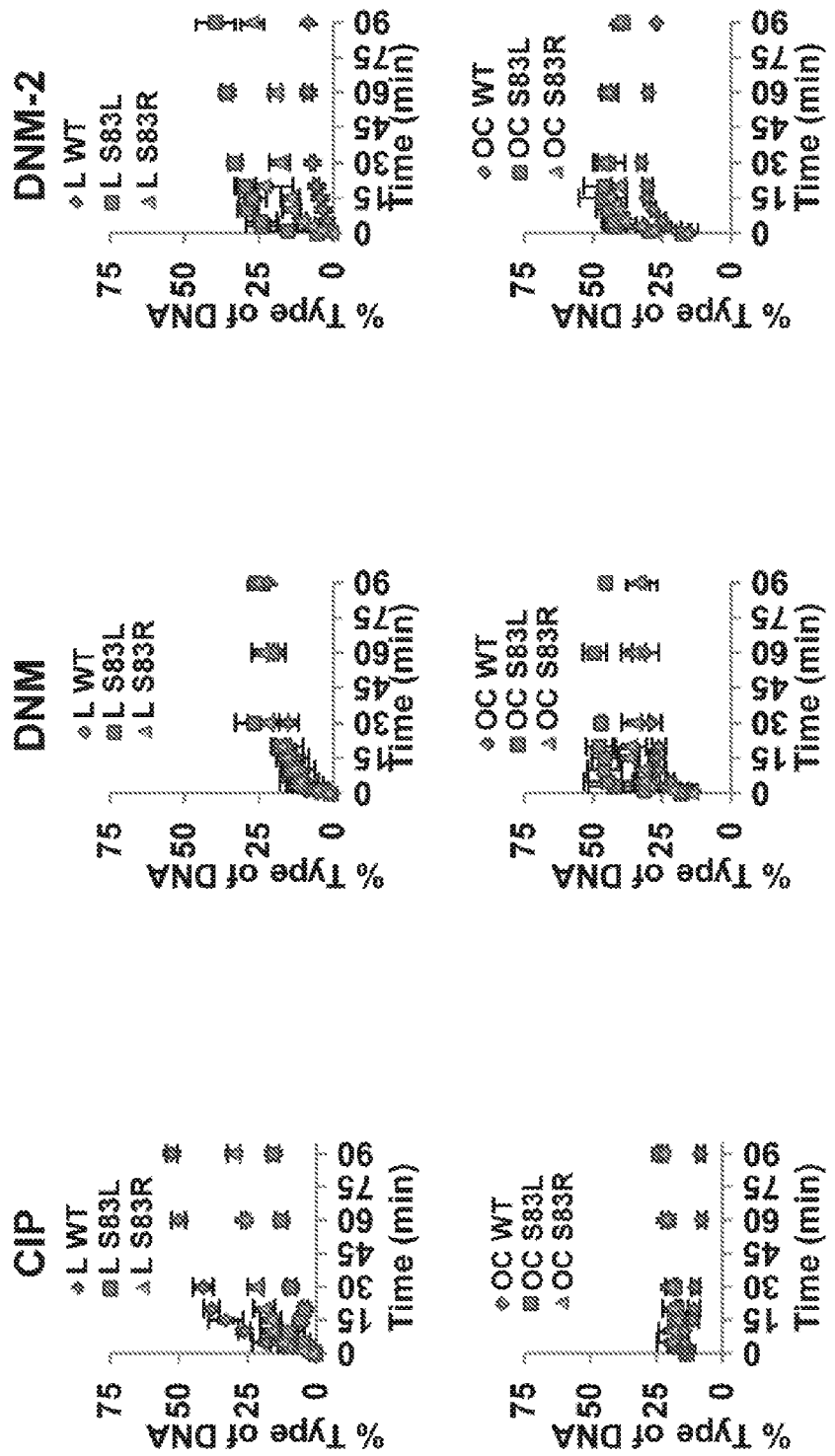
Figure 7:
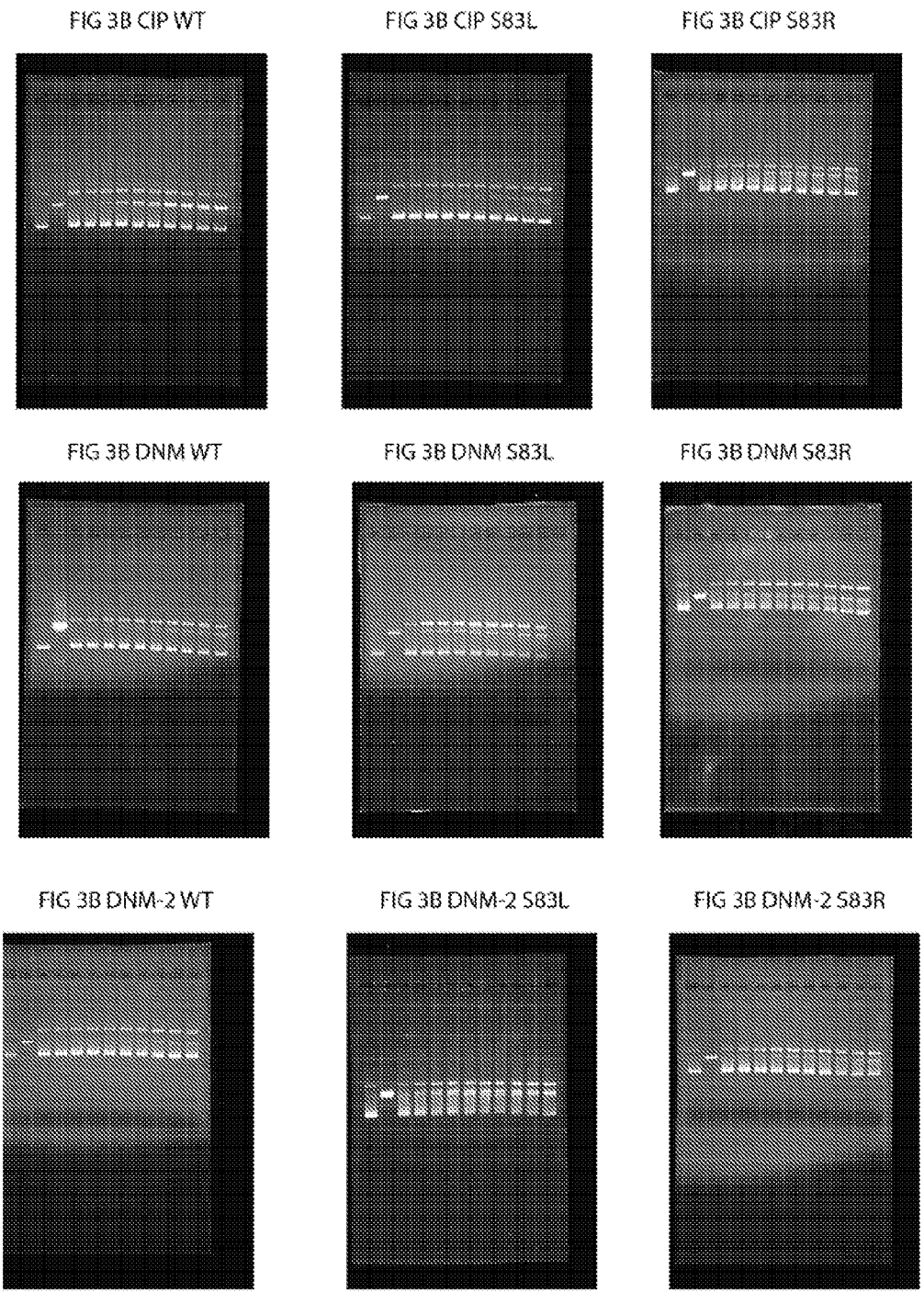
FIG. 7. Full gels from FIG. 3B.

In order to further investigate the importance of the GyrA mutation for DNM activity, the ability of DNM, DNM-2, and CIP to inhibit DNA gyrase was determined utilizing an in vitro DNA cleavage assay. In this assay, DNA gyrase is coincubated with supercoiled DNA and the compound of interest. Inhibition at the cleavage complex of DNA gyrase leads to an increase in either doubly nicked linear (L) DNA (e.g. inhibition by CIP[37]) or singly nicked open circular (OC) DNA (e.g. inhibition by GSK 299423[38]). GSK 299423 is a recently discovered DNA gyrase inhibitor that is hypothesized to stabilize the DNA-enzyme complex either pre-cleavage or after the formation of a single strand break resulting in a buildup of OC DNA[38]. Similar to previous studies, we found that CIP potently inhibits WT DNA gyrase with a greater than seven-fold increase in L DNA being observed at concentrations as low as 0.68 μM (FIG. 3A, full gels in FIG. 5, quantification in FIG. 6). Additionally, in a time course assay, inhibition of WT DNA gyrase by CIP resulted in a time dependent buildup of L DNA (FIG. 3B, full gels in FIG. 7). Alternatively when either DNM or DNM-2 was incubated with WT DNA gyrase, neither showed similar increases in L or OC DNA, suggesting that these compounds are poor inhibitors of WT DNA gyrase (FIG. 3A). Additionally, during the time course study with these compounds, buildup of L DNA was only observed at later time points and to a smaller degree (FIG. 3B and FIG. 6).

Figure 8:
FIG. 8. Cleavage assay time course with increased concentrations of CIP and DNM-2. (A) Time course of DNA cleavage of 200 µM CIP with S83L DNA gyrase. Time points were 0, 1, 3, 5, 10, 15, 20, 30, 60, and 90 min. (B) Time course of DNA cleavage of 200 µM DNM-2 with S83L DNA gyrase. Time points were 0, 1, 3, 5, 10, 15, 20, 30, 60, and 90 min. Longer time points (120 and 180 min) were also investigated with little change being observed (data not shown). One representative gel shown out of at least three independent experiments.
Figure 8:
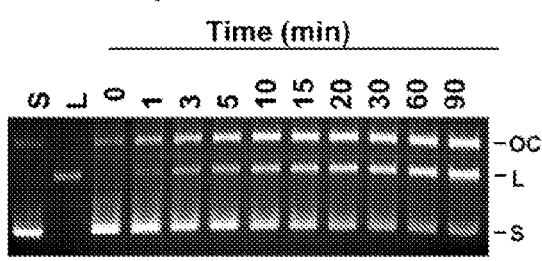
Figure 9:
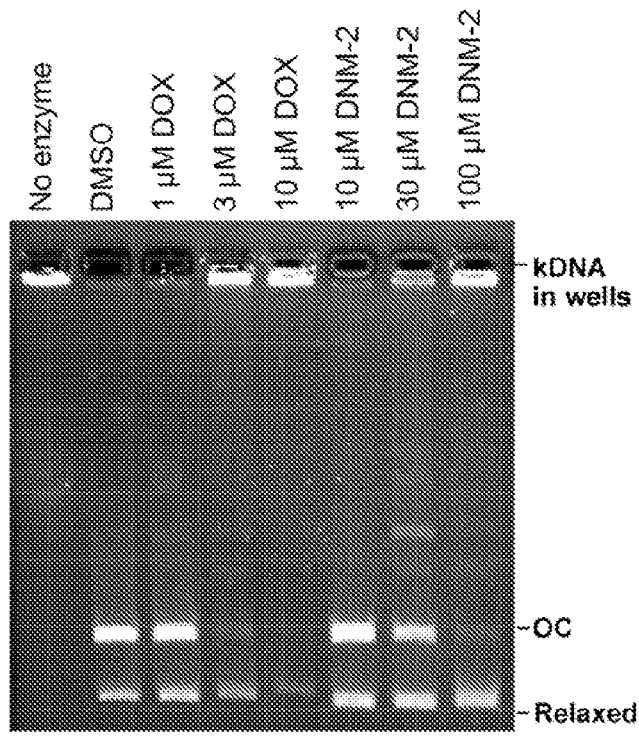
FIG. 9. Inhibition of human topoisomerase II. A decatenation assay was performed with human topoisomerase II in the presence of either DMSO, doxorubicin (DOX) or DNM-2 at the indicated concentrations. One representative gel shown out of at least three independent experiments.

The ability of CIP, DNM, and DNM-2 to inhibit S83L or S83R DNA gyrase was then determined. CIP was much less effective at inhibiting either S83L or S83R DNA gyrase compared to WT with only small increases in L DNA being observed (FIG. 3A). Additionally, minimal change was observed with 5 μM CIP at up to 1.5 h (FIG. 3B). Time course studies performed with an increased concentration of CIP (200 μM) and S83L DNA gyrase revealed a similar pattern of inhibition to that of WT DNA gyrase suggesting that the residual inhibition goes through a similar mechanism (FIG. 8A). DNM and DNM-2 induce only small increases in L DNA with S83L DNA gyrase (FIG. 3A). Instead, DNM inhibition of S83L DNA gyrase led to a significant buildup of OC DNA at 0.17 μM (P<0.05) with a similar increase observed for DNM-2 (FIG. 3A and FIG. 6). This buildup does not diminish over time (FIG. 3B) suggestive of a mode of inhibition more similar to GSK 299423 than to CIP. Increasing concentrations of DNM-2 to 200 μM and increasing the time up to 2 h confirmed that this OC buildup is not a fleeting event as occurs with CIP (FIG. 8B). DNM or DNM-2 inhibition of S83R also led to a buildup of OC DNA similar to that seen with S83L DNA gyrase only at a slightly higher concentration or longer time points, consistent with the activity of these compounds against VRE with the S83R DNA gyrase. Overall, these results are consistent with clinical isolate data, supporting the critical importance of a mutant DNA gyrase for sensitizing bacteria to DNM. Finally, in order to determine the selectivity of DNM and derivatives for bacterial DNA gyrase, a decatenation assay with human topoisomerase II was performed. While doxorubicin inhibited human topoisomerase II at concentrations as low as 3 μM, DNM-2 showed no significant inhibition at concentrations up to 30 μM (FIG. 9).

Development of Resistance to DNM.

Figure 4A:
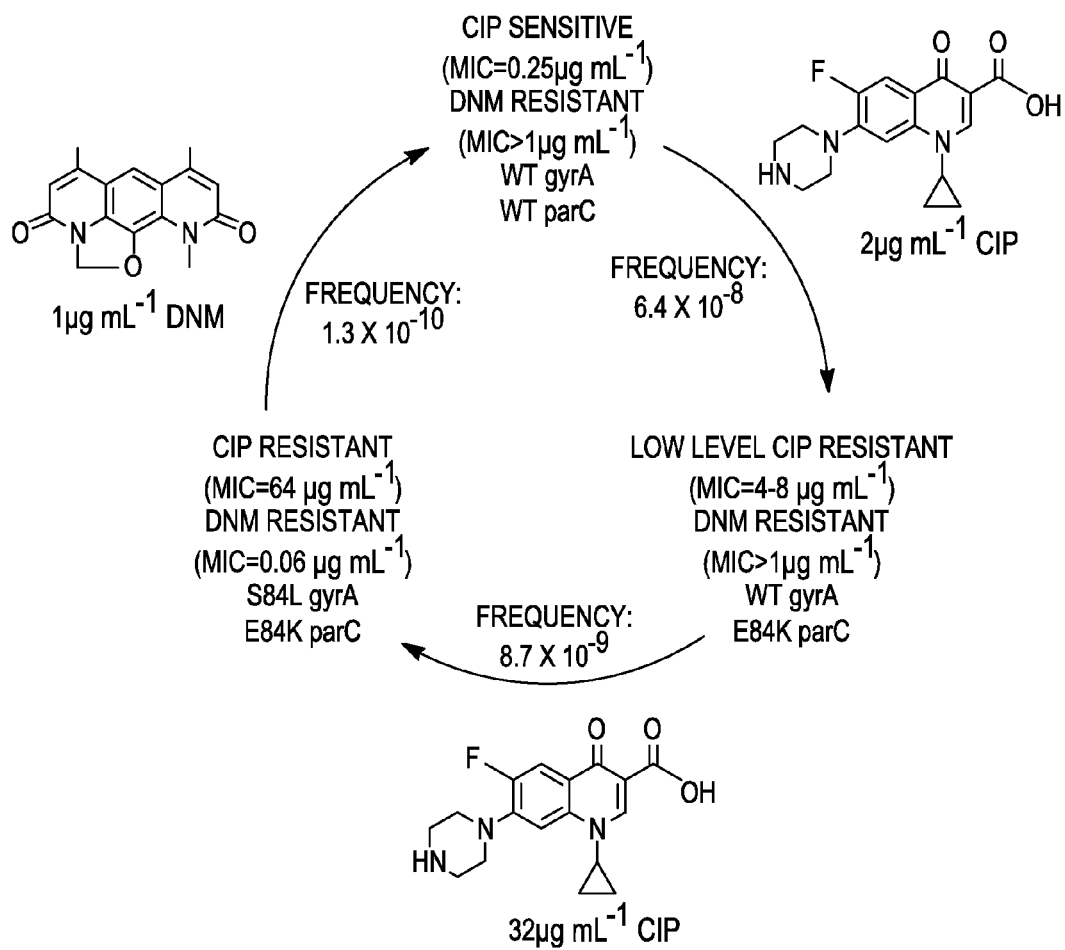
FIG. 4. Resistance mechanisms and in vivo activity. (A) Representative data of the resistance cycle observed when bacteria are sequentially treated with CIP then DNM. Each strain generated is listed with the MIC of CIP, DNM, as well as mutation status of the QRDR of GyrA and ParC shown below. The selection pressure used in each step is shown over the arrow along with the mutation frequency. (B) Kaplan-Meier curves showing the survival rates of mice infected with MRSA (NRS3, FQR). The mice received vehicle alone, 50 mg kg$^{-1}$ CIP, or 50 mg kg$^{-1}$ DNM-2 by oral gavage once-a-day for 10 days; n=15 for each group. ***P<0.005 versus vehicle and CIP, Log Rank Survival Test.
Figure 10:
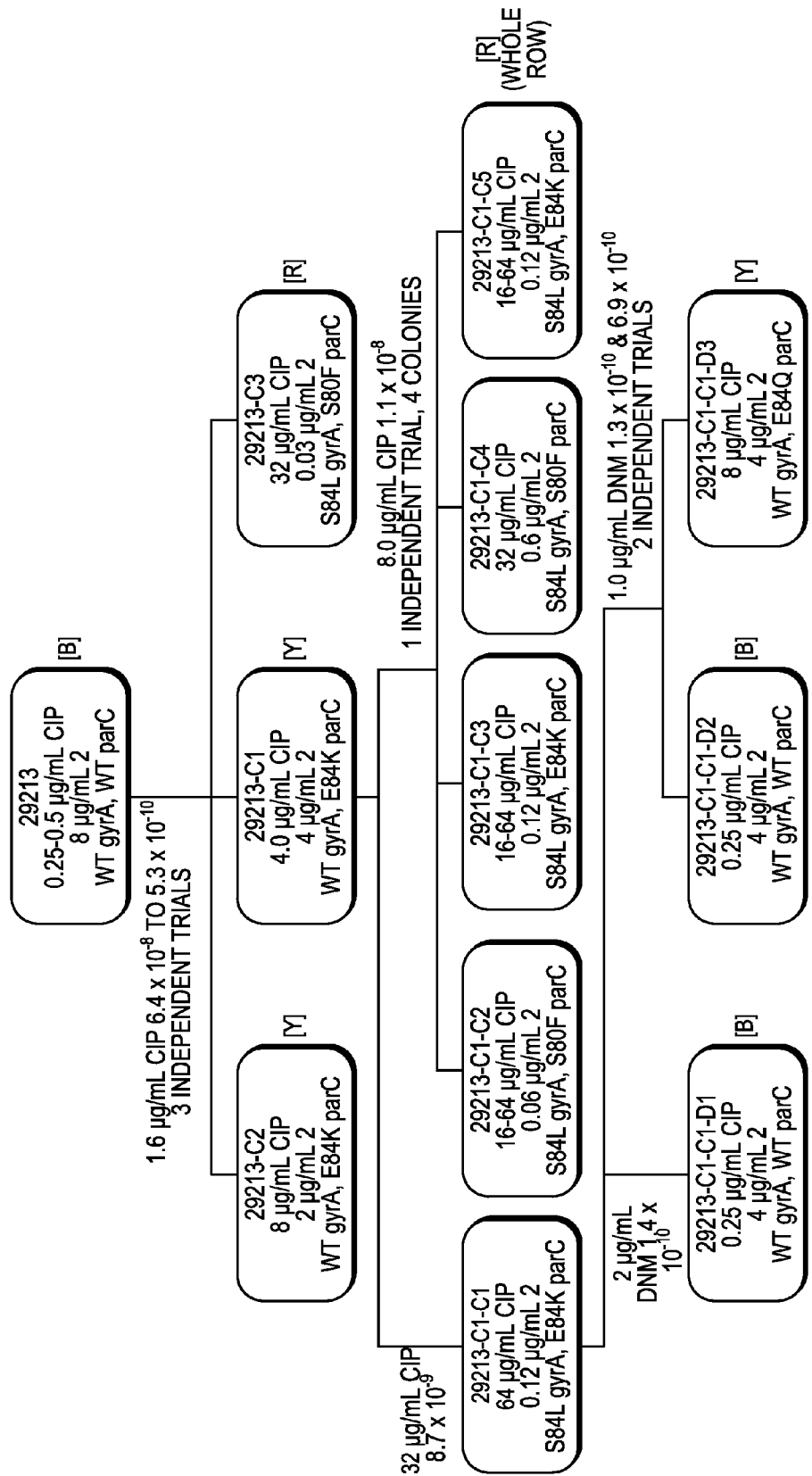
FIG. 10. Resistance cycling of CIP and DNM with S. aureus strain ATCC 29213. Conditions for selection along with resistance frequency are indicated above the boxes to which they correspond. In each box is the strain name, MIC for CIP, MIC for DNM-2, and the mutations in the QRDR of gyrA and parC. Blue (marked "[B]")=CIP sensitive (MIC<4 µg mL$^{-1}$), Yellow (marked "[Y]")=low level CIP resistance (16>MIC>4 µg mL$^{-1}$), Red (marked "[R]")=high level CIP resistance (MIC>16 µg mL$^{-1}$).

In order to explore the development of resistance to both CIP and DNM in *S. aureus*, resistant strains of ATCC 29213 were generated. Consistent with previous reports[39-40], high level resistance to CIP was generally not achieved in a single step. Instead, low level resistance (CIP MIC=4-8 μg mL$^{-1}$) was usually achieved with the first step and corresponded to a mutation in ParC (e.g. E84K or S80F, FIG. 4A, FIG. 10). Unsurprisingly, these low level resistant strains that do not have the S84L mutation in GyrA were not sensitive to DNM or DNM-2. Development of high level CIP resistance (CIP MIC=16-64 μg mL$^{-1}$) similar to what is often seen in clinical isolates[13,15,17] was observed at the second step and corresponded to an S84L mutation in GyrA. These high level CIP resistant strains were extremely sensitive to DNM (MIC=0.03-0.06 μg mL$^{-1}$) and DNM-2 (MIC=0.06-0.12 μg mL$^{-1}$). These FQR bacteria were then exposed to DNM in an effort to create DNM resistant isolates. The development of DNM resistance in high level CIP resistant strains was a rare event with resistance frequencies ranging from 1×10$^{-10}$ to 7×10$^{-10}$ (FIG. 10). When these strains were found, they showed dramatically improved sensitivity to CIP (MIC=0.25-8.0 μg mL$^{-1}$). All these strains had reverted to WT GyrA (Ser84), with the more CIP sensitive strains also having WT ParC, and the less CIP sensitive strains retaining ParC mutations (FIG. 10). This complete cycle of complementary resistance/sensitivity of CIP and DNM is shown in FIG. 4A, and the complete list of resistant strains generated and the sequences of their QRDR is in FIG. 10.

Figure 11:
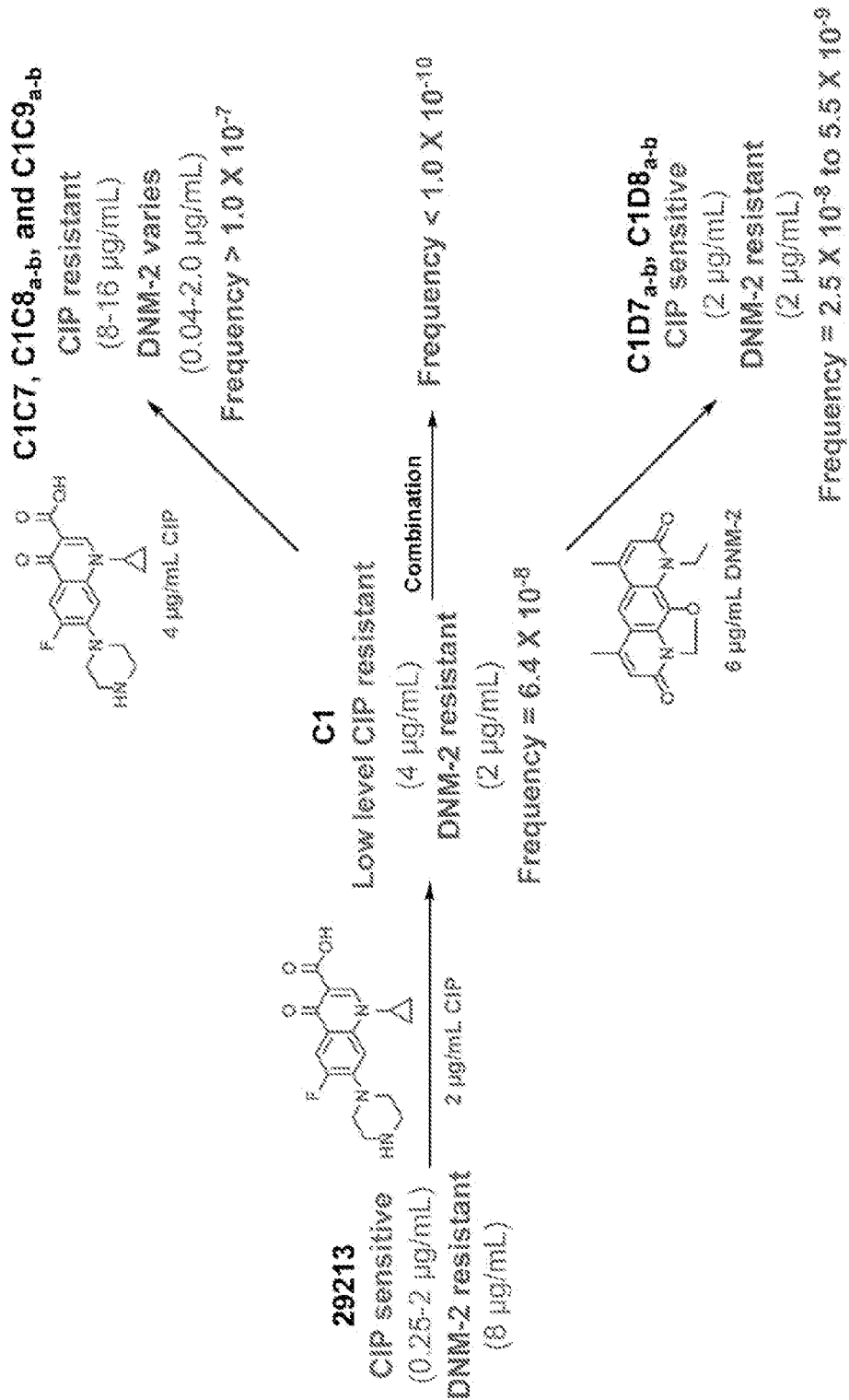
FIG. 11. Development of co-resistance to CIP and DNM-2 with S. aureus strain ATCC 29213. Initially, a low level CIP resistant mutant (C1) was generated. This strain was then treated with CIP alone, DNM-2 alone, or a combination. Along each arrow is indicated the conditions used to select for resistance. Below each strain is listed the CIP MIC, the DNM-2 MIC, and the frequency of the mutation observed.

Resistance development upon co-treatment with CIP and DNM-2 was then explored (FIG. 11). A low level CIP resistant strain (29213-C1) was utilized in these studies. Upon treatment with either CIP or DNM-2 resistant colonies were observed. However, no colonies were observed upon co-treatment (resistance frequency <1.0×10$^{-10}$).

In Vivo Efficacy of DNM-2.

Figure 12:
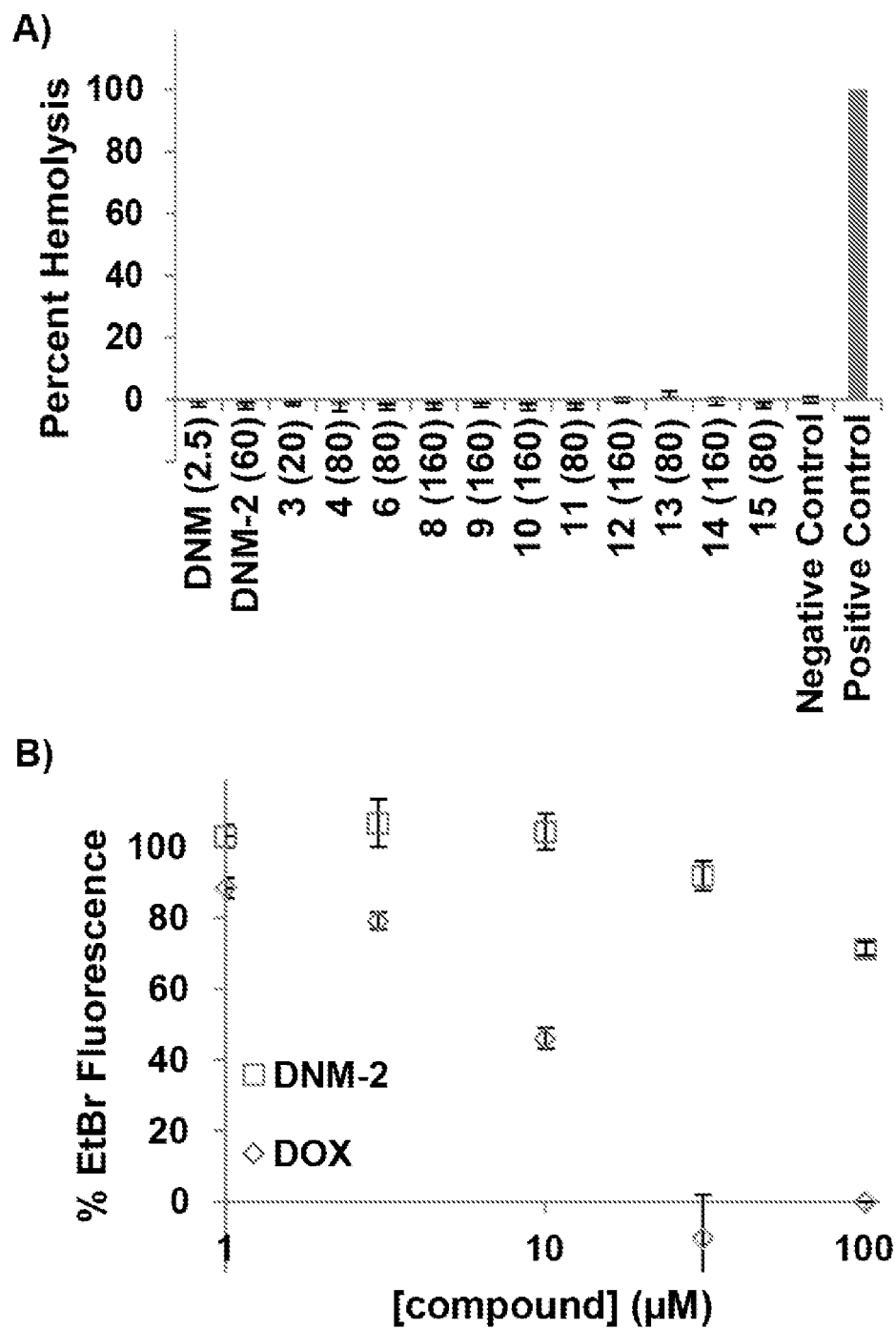
FIG. 12. In vitro toxicity. A) Hemolysis assay. Human red blood cells were co-incubated with compound. After incubation for 2 h at 37° C., the supernatant was analyzed for hemolysis. Each compound was tested either at 160 µg mL$^{-1}$ or at the highest concentration which its solubility allowed. Concentrations (µg mL$^{-1}$) are indicated in parenthesis. The negative control is DMSO and the positive control is water. Data shown is from three independent replicates±SEM. B) Ethidium bromide (EtBr) intercalation assay. Compounds were incubated with Herring Sperm DNA, ethidium bromide, and compound of interest for 30 minutes. The solutions were then analyzed for ethidium bromide fluorescence. Any decrease in percentage fluorescence is indicative of compound intercalation. Doxorubicin (DOX) was used as a positive control.

As a prelude to exploring in vivo efficacy, the toxicity and pharmacokinetic profile of DNM and key derivatives was evaluated. Treatment of red blood cells with DNM and key derivatives indicated that none of these compounds induce hemolysis (FIG. 12A). Additionally, DNM-2 demonstrated no significant DNA intercalation at concentrations up to 30

µM (FIG. 12B). This data combined with previously published data showing that deoxynybomycin is non-toxic to normal (i.e. non-cancerous) cell lines[41] suggests that these compounds would likely be well-tolerated in vivo. Treatment of mice with increasing concentrations of DNM, DNM-2, and DNM-3 showed that all three compounds were well tolerated up to the highest dose evaluated (50 mg kg$^{-1}$ by oral gavage).

Figure 13:
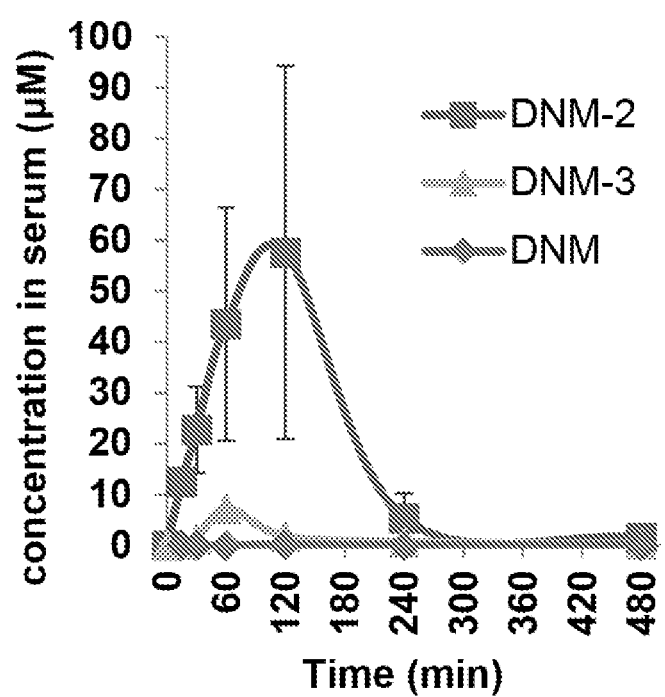
FIG. 13. Pharmacokinetic analysis of DNM, DNM-2, and DNM-3. C57/BL6 mice were treated with 50 mg kg$^{-1}$ DNM, DNM-2, or DNM-3 via oral gavage. After the indicated time points (15, 30, 60, 120, 240, and 480 min), mice were sacrificed and the serum concentrations of DNM, DNM-2, and DNM-3 was determined by HPLC.

Pharmacokinetic studies were next performed on DNM, DNM-2, and DNM-3. While DNM itself showed very low serum exposure ($C_{max}$<0.20 µM or 0.060 µg mL$^{-1}$) after a 50 mg kg$^{-1}$ oral dose, DNM-2 showed good bioavailability with a peak serum concentration of 42.6 µM (12.8 µg mL$^{-1}$) and an AUC of 44 h µg mL$^{-1}$ (FIG. 13 and Table 5). DNM-3 showed an intermediate level of bioavailability with a peak serum concentration of 4.3 µM (1.26 µg mL$^{-1}$) and an AUC of 4 h µg mL$^{-1}$. The bioavailability of these compounds mirrors the aqueous solubility suggesting that at least for this class of compounds aqueous solubility could be a reasonable predictor of oral bioavailability.

TABLE 5

Pharmacokinetic parameters for DNM, DNM-2, and DNM-3.

| | $t_{1/2}$ (hr) | AUC (hr ng mL$^{-1}$) | $C_{max}$ (ng mL$^{-1}$) | $T_{max}$ (hr) |
|---|---|---|---|---|
| DNM | | | <60 | |
| DNM-2 | 0.9 | 44000 | 12800 | 1.2 |
| DNM-3 | 1.2 | 4000 | 1260 | 1.1 |

Pharmacokinetic parameters were determined from curves presented in FIG. 13.

To explore the effect of sustained treatments in vivo, DNM-2 was administered to mice once-a-day for 10 days (via oral gavage at 50 mg kg$^{-1}$) and markers of hematological and non-hematological toxicity were examined No clinically significant evidence for myelosuppression, renal injury, or hepatic toxicity was identified (Table 6). No long-term pathologic effects were noted in the kidney, brain, lung, liver, spleen, heart, or stomach.

TABLE 6

Hematologic Toxicity of DNM-2.

| | Vehicle | DNM-2 (50 mg kg$^{-1}$) | Normal values** (Range) |
|---|---|---|---|
| RBC (×10$^6$/µL) | 7.35 ± 0.2* | 8.5 ± 0.2* | 9.07 ± 0.49 (7.77-9.77) |
| Hemoglobin (g/dL) | 12.8 ± 0.5 | 14.2 ± 0.3 | 13.4 ± 0.616 (12.0-14.5) |
| Hematocrit (%) | 38.3 ± 1 | 40 ± 1 | 44.9 ± 2.09 (39.8-48.6) |
| Platelet (cells/µL) | 330,000 ± 162,000* | 60,000 ± 10,000* | 1,310,000 ± 188,000 (990,000-1,840,000) |
| Mean Cell Volume (fl) | 52.1 ± 0.6 | 47.3 ± 0.4 | 50 ± 0.64 (49-51) |
| WBC (cells/µL) | 4970 ± 1240 | 3800 ± 300 | 5800 ± 810 (4400-7200) |
| Neutrophil (% of WBC) | 11.2 ± 4.5 | 18 ± 3 | 14 ± 7.9 (2.0-30) |
| Lymphocyte (% of WBC) | 85.2 ± 3 | 81 ± 3 | 81 ± 8.7 (60-98) |
| ALT (U/L) | 32 ± 4 | 36 ± 1 | 39 ± 7.9 (28-57) |
| ALP (U/L) | 160 ± 50 | 60 ± 10 | 72 ± 13 (40-90) |
| Albumin (g/dL) | 2.2 ± 0.2 | 3.2 ± 0.1 | 2.7 ± 0.23 (2.4-3.0) |
| Globulin (g/dL) | 2.7 ± 0.1 | 2.62 ± 0.05 | 1.2 ± 0.25 (0.8-1.5) |
| Total Bilirubin (mg/dL) | 0.43 ± 0.07 | 0.7 ± 0.1 | 0.2 ± 0.04 |
| BUN (Urea, mg/dL) | 29 ± 1 | 32.0 ± 0.4 | 29 ± 4.9 (24-40) |
| Creatine (mg/dL) | 0.17 ± 0.03 | 0.2 ± 0.0 | 0.6 ± 0.2 (0.4-1.0) |

Hematologic toxicity of DNM-2. No clinically significant evidence for myelosuppression, renal injury, or hepatic toxicity was identified in any of the treatment groups. *Platelet cell counts were low because many platelet clumps were observed. This was reflected in lower RBC counts. Total bilirubin increases were observed for both vehicle and DNM-2-treated mice due to hemolysis during blood collection. ** Normal values were reported by Schnell and Wilson (Schnell et al., Hum Gene Ther 13, 155-161, (2002)).

Figure 4B:
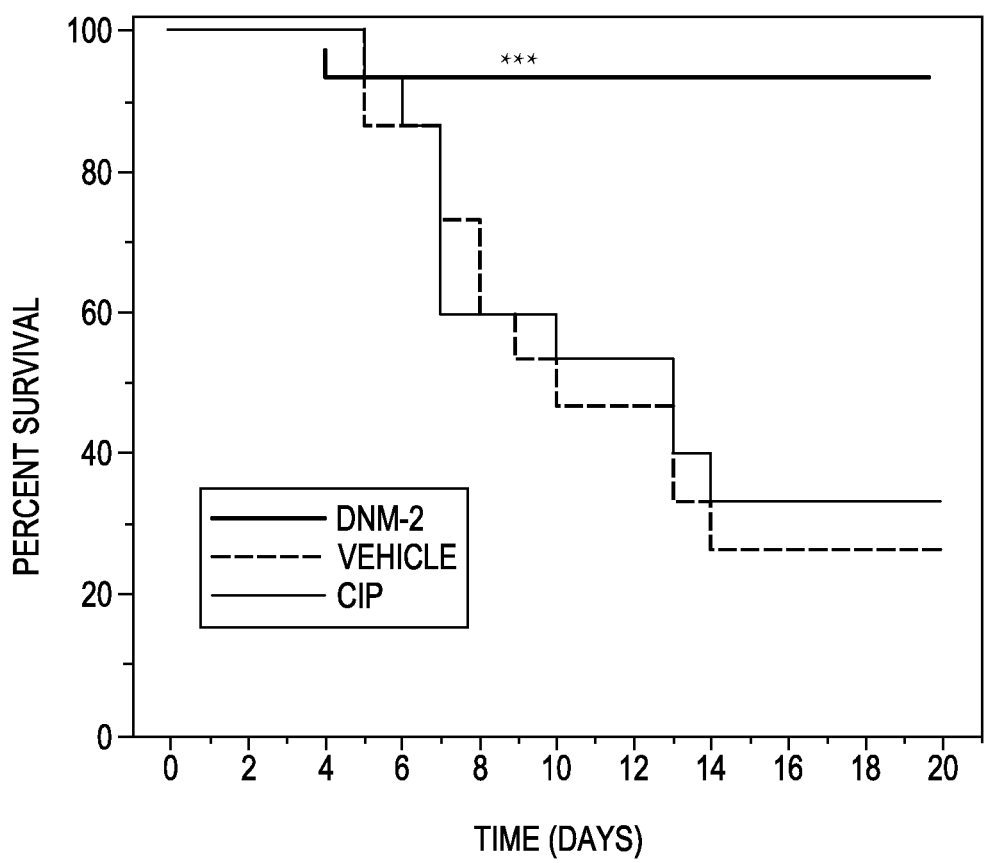
Figure 14:
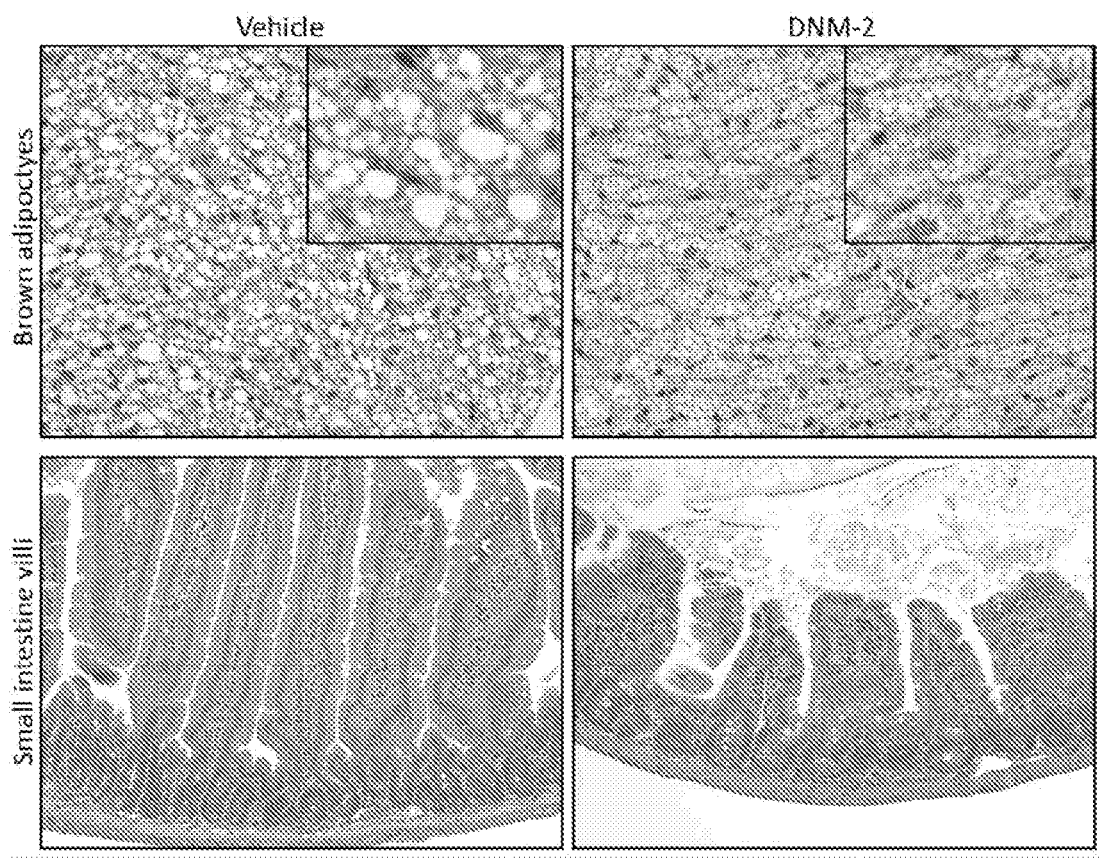
FIG. 14. In vivo toxicity studies. After euthanasia, mouse organs were collected for histopathological analyses. Tissue sections were stained with hematoxylin and eosin. All slides were systematically evaluated for evidence of acute or chronic inflammation and toxicity. No long-term pathologic effects were noted in kidneys, brains, lungs, livers, spleens, hearts, and stomachs. In small intestine sections, mild intestinal dilation associated with villi atrophy was noted. Also noted was increased vacuolation of white and brown adipocytes. These changes were considered of minimal significance.

In small intestine sections, mild intestinal dilation associated with villi atrophy was noted (FIG. 14). Also noted was increased vacuolation of white and brown adipocytes with a minimal increase in triglyceride levels. These changes were likely indirectly related to the drug, and possibly due to the antibiotic effects on the intestinal flora. As none of the mice showed any clinical symptoms, these changes were considered of minimal significance. With this indication that DNM-2 offered good exposure upon oral dosing with no observable toxicity, an in vivo model of mouse sepsis was conducted. Mice were infected with FQR MRSA (NRS3) via tail vein injection. Mice were treated with CIP (50 mg kg$^{-1}$, oral gavage), DNM-2 (50 mg kg$^{-1}$, oral gavage), or vehicle control once-a-day for 10 days. As shown by the Kaplan-Meier survival curve in FIG. 4B, mice treated with DNM-2 showed a significant survival difference relative to both CIP and vehicle treated control (P<0.005, FIG. 4B).

Discussion.

Utilizing a synthetic route building upon a palladium-catalyzed mixed cross coupling and a methylene bridge insertion, hundreds of milligrams of the natural product DNM were prepared as described herein. The modular nature of the synthesis also allows access to non-natural DNM derivatives, many of which display similar antibacterial efficacy but with significantly better solubility properties than the parent. Specifically, small alkyl appendages greatly improve aqueous solubility: DNM has aqueous solubility of only 9 μM compared to 121 μM for DNM-2. This improved solubility is likely due to the ability of the short alkyl chains to break up π-stacking similarly to what was observed with derivatives of DNQ[36,42]. Longer or more alkyl chains do not display similar increases in aqueous solubility likely due to the increased hydrophobicity of these compounds. With these compounds in hand, a structure-activity relationship was established and derivatives were found to have comparable potencies to the parent against FQR MRSA and VRE in cell culture and against mutated DNA gyrase in vitro.

The major mechanism of FQR for bacteria involves the mutation of FQ targets DNA gyrase and topoisomerase IV. While nearly all FQR bacteria found to date have such mutations, the exact mutation can vary based on the bacterium. For MRSA, nearly 100% have the S84L mutation in DNA gyrase[13-21]. Similarly, B. anthracis, E. coli, and A. baumannii also have the analogous serine mutated to leucine[43-45]. In VRE the serine is mutated to multiple different residues (Ile, Arg, and Tyr) while in S. pneumoniae, K. pneumonia, and N. gonorrhoeae this Ser is often changed to either Phe or Tyr[22-26,46-48]. P. aeruginosa differs in that it naturally has a Thr instead of the Ser. However, P. aeruginosa is similar to VRE in that the Thr is mutated to an Ile in FQR strains. We now show that DNM has excellent activity versus Ser→Leu or Ser→Ile mutants with moderate activity in Ser→Arg strains, with these cell culture results correlating with the potencies of the compounds in in vitro assays with DNA gyrase and mutants. The ability of DNM to target these different mutants suggests that this natural product or its derivatives could be broadly applicable against FQR bacteria regardless of the exact nature of the Ser mutation.

Figure 3:
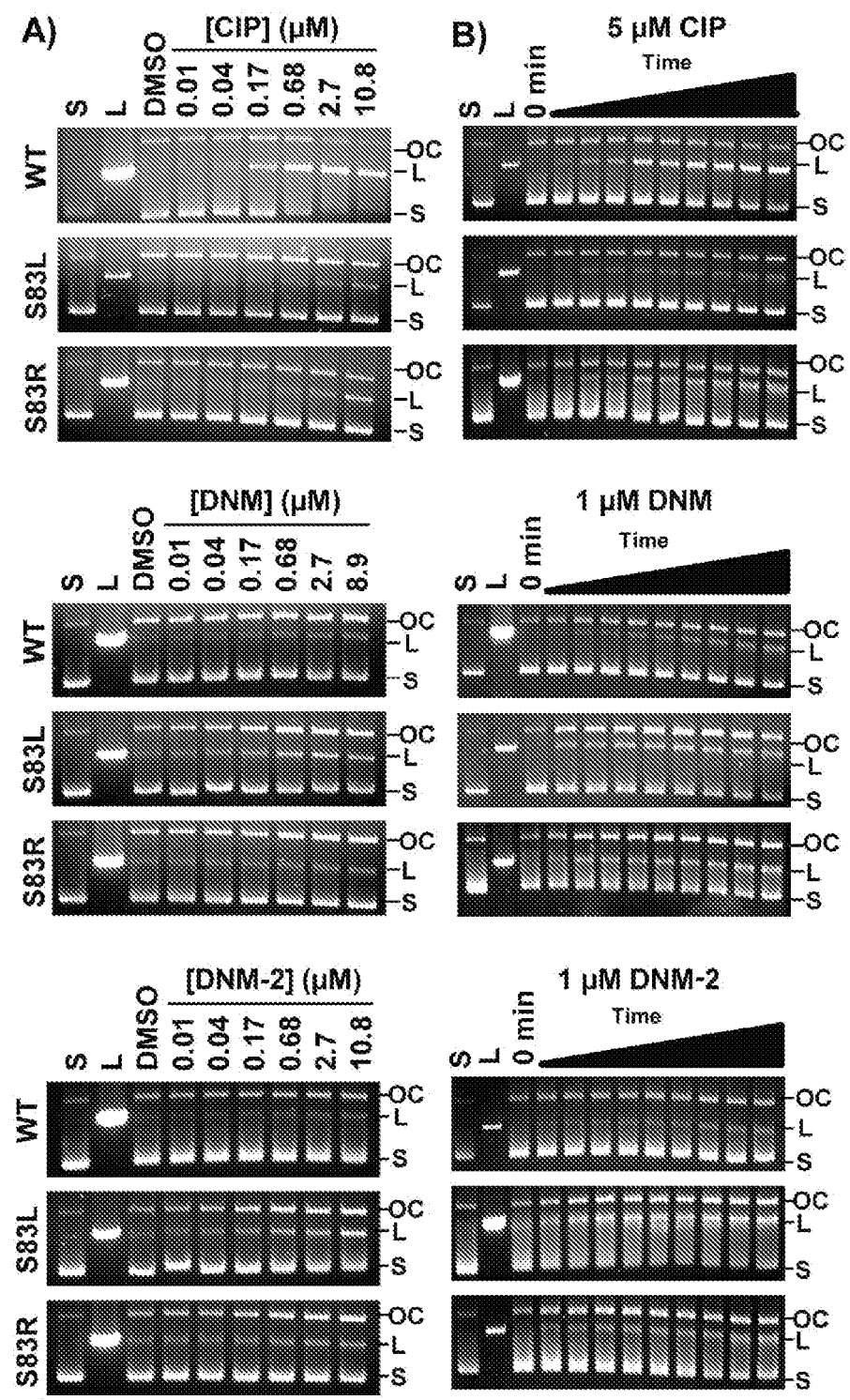
FIG. 3. Inhibition of WT and mutant DNA gyrase. (A) DNA cleavage assay with WT, S83L, and S83R *E. coli* DNA gyrase in the presence of increasing concentrations of CIP, DNM, and DNM-2 (top, middle, and bottom, respectively). Concentrations were 0.01, 0.04, 0.017, 0.68, 2.7, and 10.8 µM except for DNM which was 8.9 µM for the highest concentration. S=supercoiled, L=linear, and OC=open circular or nicked DNA. (B) Timecourse of DNA cleavage with WT, S83L and S83R *E. coli* DNA gyrase in the presence of 5 µM CIP, 1 µM DNM, and 1 µM DNM-2 (top, middle, and bottom, respectively). Timepoints were 0, 1, 3, 5, 10, 15, 20, 30, 60, and 90 min. All gels are representative data from at least three independent experiments.

FQs inhibit DNA gyrase causing double stranded breaks that appear as a buildup of L DNA in a DNA gyrase cleavage assay (FIG. 3 and Kampranis & Maxwell[37]). Maxwell and coworkers have demonstrated that FQs initially stabilize a single phosphotyrosine bond as evidenced by an initial buildup of OC DNA,[37] also observed in FIG. 3B. However, the FQ stabilization of a single strand break causes an even faster second cleavage event that is also stabilized by FQs thus explaining the rapid buildup of linear DNA[37]. Another DNA gyrase inhibitor, GSK299423, acts via a different mechanism[38]. Unlike FQs that bind within the two active sites, it binds between the active sites stabilizing either an uncleaved or a single-stranded cleaved DNA. The stabilization induced by GSK299423 differs from that of CIP in that it does not result in a second cleavage event and instead causes a buildup of OC DNA. The more potent activity of DNM against FQR mutant DNA gyrase suggests that DNM likely binds similarly to FQs, near the mutated residues and thus near the two active sites. Despite this similarity in binding position, the phenotype of DNM in the DNA cleavage assay (i.e. the buildup of OC DNA) suggests that its overall mode of inhibition is more similar to that of GSK299423. The mutational status of ParC does not affect sensitivity to DNM, as shown by the data from the clinical isolates and resistance mutants.

In this study, we showed that an entire resistance/sensitization cycle is possible beginning with S. aureus (ATCC 29213) that is FQS/DNM resistant. After multiple rounds of selection against CIP, a FQR/DNM sensitive strain was generated. Then, after a selection round with DNM, a FQS/DNM resistant strain was found. These results suggest intriguing clinical possibilities for DNM, either alone or in combination with FQs. As surveillance data shows the ubiquity of FQR in MRSA and VRE, a DNM compound could be an outstanding therapeutic option for these infections; indeed, a new orally available treatment for MRSA and VRE is a well-recognized clinical need[49] and would be a welcome addition to the antibiotic arsenal. As resistance to DNM emerges, the data predict that such bacteria would be sensitive to FQs. At this point, a diagnostic test could be used to choose between FQ or DNM, or a co-treatment with both a FQ and DNM would be possible. As reported herein, co-resistance was not generated in cell culture, with no colonies being observed upon treatment with 4 μg mL$^{-1}$ CIP and 6 μg mL$^{-1}$ DNM-2.

Before this study, little to no data existed about the administration of DNM to animals. However, a related but less potent compound nybomycin (C=CH$_2$OH) has been examined in mice. It was found to be well tolerated when dosed either subcutaneously, orally, or by IP injection[27]. However, it showed no activity in mice infected with various bacteria (K. pneuomoniae, S. aureus, or M. tuberculosis), leading Brock and Sokolski to suggest that this high tolerability and lack of efficacy is likely a result of the very poor solubility of nybomycin (similar to DNM it is only soluble in concentrated acid) and thus lack of absorption[27]. We demonstrated that DNM also has a high Maximal Tolerated Dose (MTD) (>50 mg kg$^{-1}$ oral gavage), but pharmacokinetic analysis indicate that it is not absorbed to any appreciable degree. However, DNM-2, which has improved solubility, was also very well tolerated (MTD>50 mg kg$^{-1}$) and showed favorable pharmacokinetic properties when dosed orally. Additionally, in this study we found that orally administered DNM-2 is effective in treating mice infected with MRSA, thus showing the first in vivo efficacy for this class of compounds.

FQR pathogens are now a significant medical problem, and the data presented herein reveal the considerable translational potential of DNM derivatives, including the following five points: 1) A short and efficient synthetic route has been developed that can readily supply large amounts of compound. 2) DNM-2 has outstanding PK properties with a peak serum concentration (~50 μM when given at 50 mg kg$^{-1}$ orally) far exceeding the MIC. 3) DNM-2 is extremely well-tolerated in mice with no signs of toxicity at the dose levels tested. This is consistent with our data showing these compounds do not induce hemolysis or inhibit human topoisomerase II. 4) DNM-2, when given orally, has outstanding efficacy in a mouse model of MRSA infection. An oral drug for MRSA and VRE is a well-recognized clinical need, and DNM-2 has tremendous promise in this regard. 5) Finally, resistance to DNM is much more difficult than resistance to cipro, as shown by the resistance frequencies in FIG. 4A. A problem with novel antibacterials is that bacterial resistance typically necessitates the development of a new drug to treat those drug-resistant pathogens. However, when the inevitable resistance to DNM/derivatives does arise clinically, these bacteria will be sensitive to FQs, a widely used and well-understood class of antibiotics.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating a bacterial infection in a mammal, which involve administering to a mammal having a bacterial infection an effective amount of a compound or composition described herein. A mammal includes a primate, human, rodent, canine, feline, bovine, ovine, equine, swine, caprine, bovine and the like.

The ability of a compound of the invention to treat a bacterial infection may be determined by using assays well known to the art. For example, the design of treatment protocols, toxicity evaluation, data analysis, quantification of cell kill, and the biological significance of the use of relevant bacterial screens are known. In addition, ability of a compound to treat a bacterial infection may be determined using the tests as described or referenced herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthesis of DNM and Derivatives

Synthesis of the diazaanthracenols of DNM and the derivatives were performed as described below. General chemical reagents were purchased from Sigma Aldrich. Metal catalysts and ligands were purchased from Strem Chemicals Inc. (Newburyport, Mass.). Alkynes were purchased from GFS Chemicals (Powell, Ohio) and bis-pina-colboronate was purchased from Frontier Scientific (Logan, Utah). All reagents were used without further purification unless otherwise noted. $^1$H-NMR and $^{13}$C-NMR spectra were recorded on Varian Unity spectrometers at 500 MHz and 125 MHz, respectively. Spectra generated from a solution of CDCl$_3$ were referenced to residual chloroform ($^1$H: δ 7.26 ppm, $^{13}$C: δ 77.16 ppm). Spectra generated in mixtures of CDCl$_3$ and CD$_3$OD were referenced to CD$_3$OD ($^1$H: δ 3.31 ppm, $^{13}$C: δ 49.0 ppm).

General Protocol A: Synthesis of Diazaanthracenols.

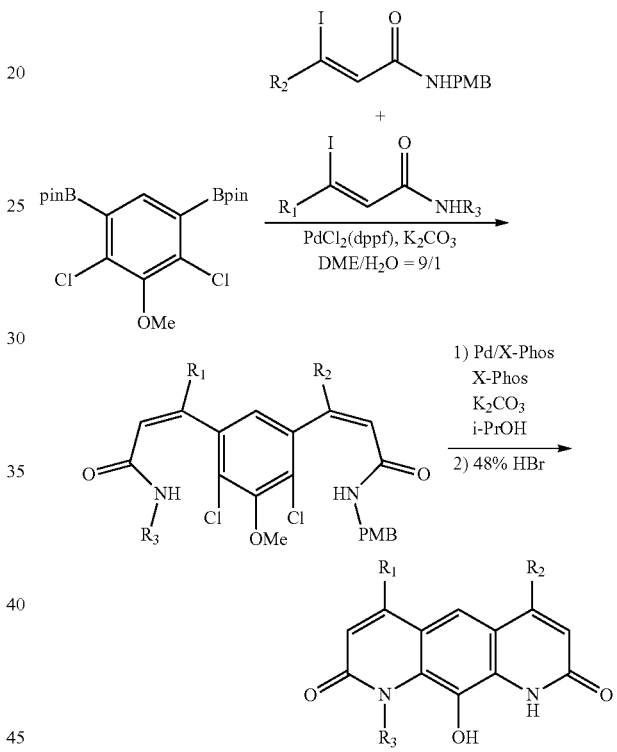

The synthesis of these diazaanthracenols has been previously described by Hergenrother and co-workers (Bair et al., *J. Am. Chem. Soc.* 132, 5469-5478, (2010); Parkinson et al., *ACS Chem Biol* 8, 2173-2183, (2013)). The only alteration from these protocols was that the phenols were further purified by reversed phase chromatography (10:90 MeCN:H$_2$O to 100:0 MeCN:H$_2$O) using a CombiFlash Rf (Teledyne Isco).

General Protocol B: Synthesis of Deoxynybomycins.

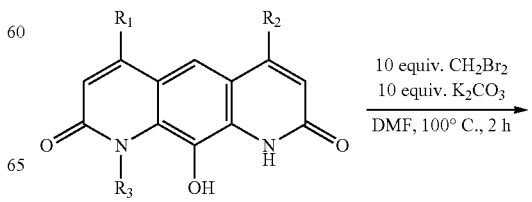

-continued

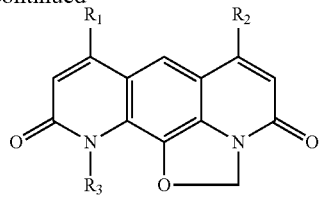

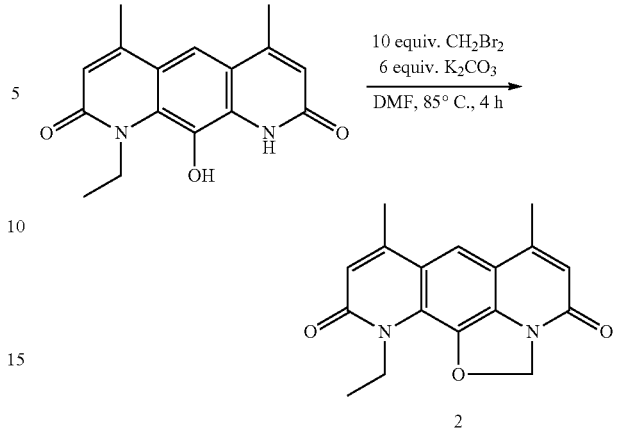

To a 20-mL vial was added diazaanthracenol (1 equiv.) and potassium carbonate (10 equiv.). The vial was evacuated and filled with argon three times. Degassed DMF (90 mL per mmol diazaanthracenol) was added followed by dibromomethane (10 equiv.). The only difference was with 5 in which 100 equiv of 1,1-dibromoethane were used in place of the dibromomethane. The vial was plunged into an oil bath preheated to 100° C. The reaction was monitored by TLC (10% MeOH in $CH_2Cl_2$) with starting material appearing under UV as a green spot at the baseline and product appearing under UV as a bright blue spot at $R_f$=0.5. When starting material was no longer visible by TLC (usually after 2-3 h), the solvent was evaporated and the residue was purified by silica gel chromatography (0 to 5% MeOH in $CH_2Cl_2$). DNM and derivatives were collected as off-white solids.

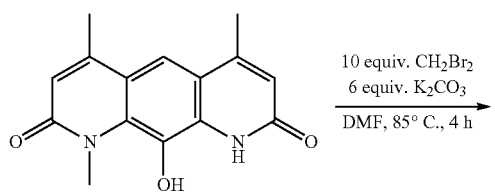

DNM

Synthesized from bispinacolborane, (Z)-3-iodo-N-(4-methoxybenzyl)but-2-enamide, and (Z)-3-iodo-N-methyl-but-2-enamide (see Bair et al *J. Am. Chem. Soc.* 132, 5469-5478, (2010)), by General Protocols A and B. 73% yield for methylene bridge insertion. 16% yield over 4 steps. 11% overall yield from commercially available starting material. Product is an off-white solid. $^1$H NMR (2:1 $CDCl_3$: $CD_3OD$, 400 MHz) δ 7.55 (s, 1H, aryl CH), 6.49 (d, 1H, J=1.0 Hz, vinyl CH), 6.47 (d, 1H, J=1.0 Hz, vinyl CH), 6.39 (s, 2H, $OCH_2N$), 3.92 (s, 3H, $NCH_3$), 2.54 (d, 3H, J=1.0 Hz, allylic $CH_3$), 2.52 (d, 3H, J=1.0 Hz, allylic $CH_3$). HRMS (ESI-TOF) calcd for $C_{16}H_{15}N_2O_3$ (M+H)$^+$: 283.1094, found: 283.1083. Melting Point: >350° C., 358-360° C. resulted in decomposition. IR (cm$^{-1}$): 1651 (s), 1625 (s), 1593 (s), 1558 (s), 1485 (m), 1445 (m), 1351 (s), 1327 (m), 1291 (w), 1154 (w).

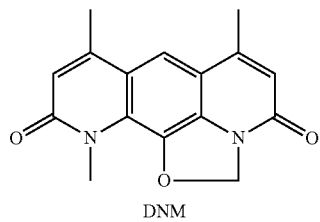

2

Synthesized from bispinacolborane, (Z)-3-iodo-N-(4-methoxybenzyl)but-2-enamide, and (Z)-N-ethyl-3-iodobut-2-enamide (Parkinson et al., *ACS Chem Biol* 8, 2173-2183, (2013)), by General Protocols A and B. 64% yield for methylene bridge insertion. 11% yield over 4 steps. Product is an off-white solid. $^1$H NMR ($CDCl_3$, 500 MHz) δ 7.47 (s, 1H, aryl CH), 6.52 (d, 1H, J=1.0 Hz, vinyl CH), 6.46 (d, 1H, J=1.0 Hz, vinyl CH), 6.40 (s, 2H, $OCH_2N$), 4.54 (q, 2H, J=7.0 Hz, $NCH_2CH_3$), 2.52 (d, 3H, J=1.0 Hz, allylic $CH_3$), 2.50 (d, 3H, J=1.0 Hz, allylic $CH_3$), 1.36 (t, 3H, J=7.0 Hz). $^{13}$C NMR ($CDCl_3$, 125 MHz) δ 161.63, 158.64, 147.63, 146.74, 135.05, 132.32, 125.06, 121.34, 121.05, 120.79, 113.62, 113.42, 86.10, 40.27, 20.34, 18.00, 14.96. HRMS (ESI-TOF) calcd for $C_{17}H_{17}N_2O_3$ (M+H)$^+$: 297.1239 found: 297.1246. Melting Point: >250° C., 253-255° C. resulted in decomposition. IR (cm$^{-1}$): 1668 (m), 1657 (s), 1625 (s), 1596 (s), 1561 (m), 1485 (w), 1447 (2) 1419 (w), 1394 (m), 1380 (m), 1351 (s), 1322 (m), 1282 (w), 1243 (w), 1148 (w).

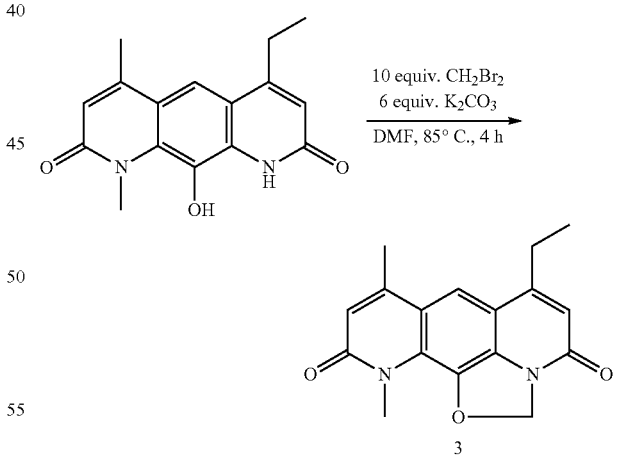

3

Synthesized from bispinacolborane, (Z)-3-iodo-N-(4-methoxybenzyl)pent-2-enamide, and (Z)-3-iodo-N-methyl-but-2-enamide, by General Protocols A and B. 72% yield for methylene bridge insertion. 13% yield over 4 steps. Product is an off-white solid. $^1$H NMR ($CDCl_3$, 500 MHz) δ 7.47 (s, 1H, aryl CH), 6.50 (d, 1H, J=1.0 Hz, vinyl CH), 6.47 (d, 1H, J=1.0 Hz, vinyl CH), 6.37 (s, 2H, $OCH_2N$), 3.91 (s, 3H, $NCH_3$), 2.90 (q, 2H, J=7.5 Hz, allylic $CH_2H_3$), 2.47 (s, 3H, allylic $CH_3$), 1.37 (t, 3H, J=7.5 Hz, allylic $CH_2CH_3$). $^{13}$C NMR (CDCl$_3$, 125 MHz) δ 161.98, 158.86, 153.03, 146.76, 135.79, 132.48, 125.65, 120.71, 120.50, 119.43, 113.05, 112.86, 86.03, 32.60, 24.46, 20.27, 12.82. HRMS (ESI-TOF) calcd for C$_{17}$H$_{17}$N$_2$O$_3$ (M+H)$^+$: 297.1239 found: 297.1247. Melting Point: >250° C., 274-275° C. resulted in decomposition. IR (cm$^{-1}$): 1675 (w), 1658 (s), 1631 (s), 1598 (m), 1559 (w), 1491 (w), 1440 (w), 1414 (m), 1383 (w), 1342 (w), 1291 (2), 1147 (w).

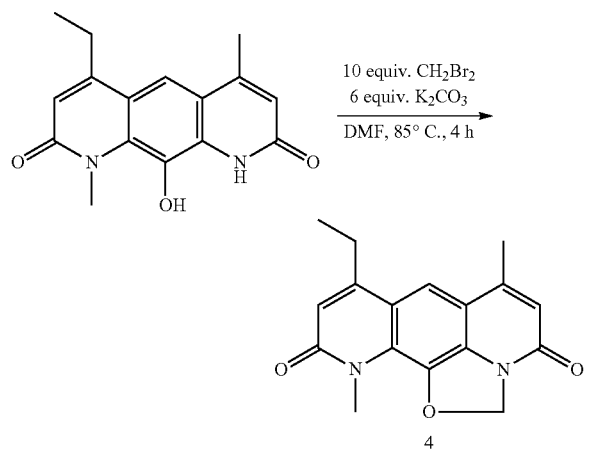

Synthesized from bispinacolborane, (Z)-3-iodo-N-(4-methoxybenzyl)but-2-enamide, and (Z)-3-iodo-N-methyl-pent-2-enamide, by General Protocols A and B. 2% yield over 4 steps. Product is an off-white solid. $^1$H NMR (CDCl$_3$, 500 MHz) δ 7.51 (s, 1H, aryl CH), 6.53 (d, 1H, J=1.0 Hz, vinyl CH), 6.46 (d, 1H, J=1.0 Hz, vinyl CH), 6.38 (s, 2H, OCH$_2$N), 3.94 (s, 3H, NCH$_3$), 2.88 (q, 2H, J=7.5 Hz, allylic, CH$_2$H$_3$), 2.51 (d. 3H, J=1.0 Hz, allylic CH$_3$), 1.36 (t, 3H, J=7.5 Hz, allylic CH$_2$CH$_3$). $^{13}$C NMR (CDCl$_3$, 125 MHz) δ 162.38, 158.69, 151.94, 147.66, 135.89, 132.29, 126.09, 121.53, 120.09, 118.50, 113.56, 112.87, 86.15, 32.71, 25.95, 18.06, 12.93. HRMS (ESI-TOF) calcd for C$_{17}$H$_{17}$N$_2$O$_3$ (M+H)$^+$: 297.1239 found: 297.1234. Melting Point: >250° C., 269-270° C. resulted in decomposition. IR (cm$^{-1}$): 1651 (s), 1621 (s), 1594 (s), 1557 (w), 1490 (w), 1421 (m), 1354 (m), 1328 (m), 1292 (w), 1154 (w).

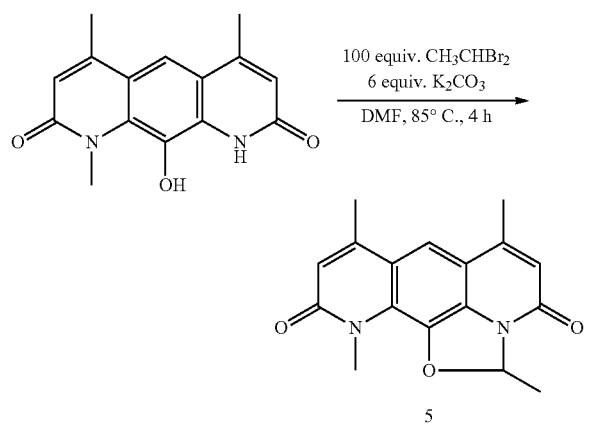

Synthesized from bispinacolborane, (Z)-3-iodo-N-(4-methoxybenzyl)but-2-enamide, and (Z)-3-iodo-N-methyl-but-2-enamide, by General Protocols A and B. General Protocol B was altered slightly. Specifically, 1,2-dibromoethane was used in place of dibromomethane and 100 equivalents were used instead of 10. 4% yield over 4 steps. Product is a yellow/off-white solid. $^1$H NMR (CDCl$_3$, 500 MHz) δ 7.43 (s, 1H, aryl CH), 6.80 (q, 1H, J=5.5 Hz, OCHN), 6.51 (d, 1H, J=1.0 Hz, vinyl CH), 6.44 (d, 1H, J=1.0 Hz, vinyl CH), 3.93 (s, 3H, NCH$_3$), 2.50 (d, 3H, J=1.0 Hz, allylic CH$_3$), 2.49 (d, 3H, J=1.0 Hz, allylic CH$_3$), 1.96 (d, 3H, J=5.5 Hz). $^{13}$C NMR (CDCl$_3$, 125 MHz) δ 163.09, 159.71, 148.92, 148.49, 135.09, 132.19, 125.52, 121.65, 121.45, 119.96, 114.40, 113.74, 96.44, 32.99, 20.34, 20.22, 17.92. HRMS (ESI-TOF) calcd for C$_{17}$H$_{17}$N$_2$O$_3$ (M+H)$^+$: 297.1239 found: 297.1244.

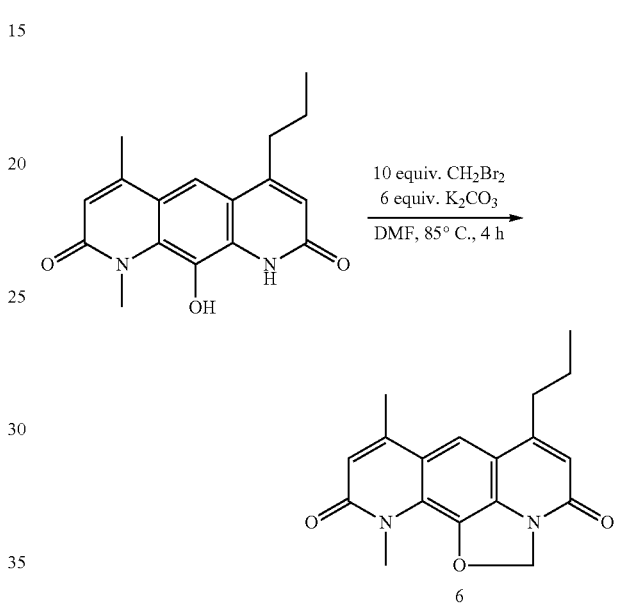

Synthesized from bispinacolborane, (Z)-3-iodo-N-(4-methoxybenzyl)hex-2-enamide, and (Z)-3-iodo-N-methyl-but-2-enamide, by General Protocols A and B. 2% yield over 4 steps. Product is an off-white solid. $^1$H NMR (CDCl$_3$, 500 MHz) δ 7.48 (s, 1H, aryl CH), 6.52 (1H, vinyl CH), 6.46 (1H, vinyl CH), 6.39 (s, 2H, OCH$_2$N), 3.93 (s, 3H), 2.83 (t, 2H, J=7.5 Hz), 2.49 (3H, allylic CH$_3$), 1.80 (m, 2H), 1.06 (t, 3H, J=7.5 Hz). $^{13}$C NMR (CDCl$_3$, 125 MHz) δ 162.01, 158.76, 151.62, 146.73, 135.84, 132.60, 125.70, 120.74, 120.55, 120.40, 113.24, 113.01, 86.06, 33.39, 32.61, 21.96, 20.24, 14.05. HRMS (ESI-TOF) calcd for C$_{18}$H$_{19}$N$_2$O$_3$ (M+H)$^+$: 311.1396 found: 311.1405. Melting Point: >200° C., 228-230° C. resulted in decomposition. IR (cm$^{-1}$): 1660 (s), 1636 (s), 1600 (s), 1558 (w), 1489 (w), 1442 (w), 1416 (w), 1382 (w), 1344 (m), 1277 (w), 1148 (w).

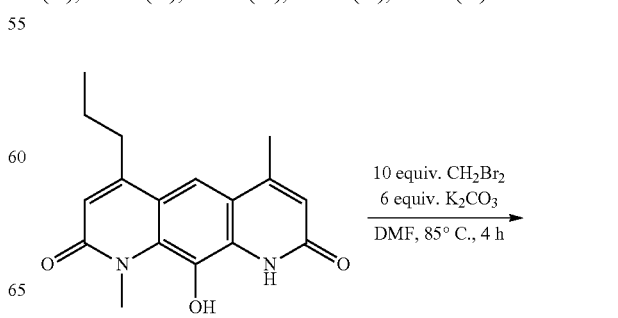

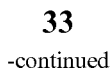

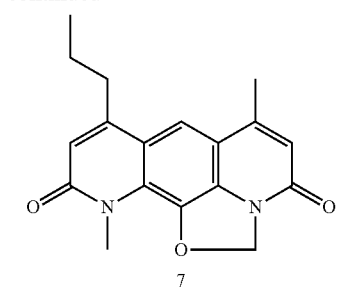

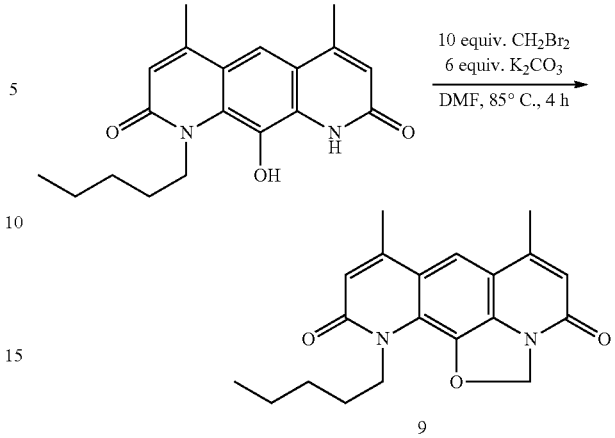

Synthesized from bispinacolborane, (Z)-3-iodo-N-(4-methoxybenzyl)but-2-enamide, and (Z)-3-iodo-N-methyl-hex-2-enamide, by General Protocols A and B. 1% yield over 4 steps. Product is an off-white solid. $^1$H NMR (CDCl$_3$, 500 MHz) δ 7.51 (s, 1H, aryl CH), 6.52 (d, 1H, J=1.0 Hz, vinyl CH), 6.46 (d, 1H, J=1.0 Hz, vinyl CH), 6.39 (s, 2H, OCH$_2$N), 3.95 (s, 3H), 2.81 (t, 2H, J=7.5 Hz), 2.52 (d, 3H, J=1.0 Hz, allylic CH$_3$), 1.78 (m, 2H), 1.07 (t, 3H, J=7.5 Hz). $^{13}$C NMR (CDCl$_3$, 125 MHz) δ 162.16, 158.61, 150.46, 147.57, 135.82, 132.19, 126.09, 121.43, 120.03, 119.38, 113.46, 113.01, 86.07, 34.98, 32.64, 21.83, 17.97, 14.19. HRMS (ESI-TOF) calcd for C$_{18}$H$_{19}$N$_2$O$_3$ (M+H)$^+$: 311.1396 found: 311.1393.

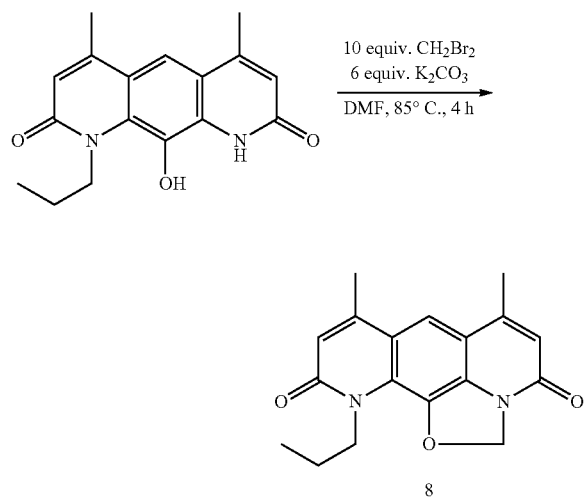 [SMILES: CCn1c(=O)cc(C)c2cc3c(C)cc(=O)[nH]c3c(O)c21 ; CCn1c(=O)cc(C)c2cc3c(C)cc(=O)n4c3c(c21)OC4]

Synthesized from bispinacolborane, (Z)-3-iodo-N-(4-methoxybenzyl)but-2-enamide, and (Z)-3-iodo-N-propyl-but-2-enamide, by General Protocols A and B. 2% yield over 4 steps. Product is an off-white solid. $^1$H NMR (CDCl$_3$, 500 MHz) δ 7.46 (s, 1H, aryl CH), 6.51 (1H, vinyl CH), 6.46 (1H, vinyl CH), 6.39 (s, 2H, OCH$_2$N), 4.42 (m, 2H), 2.52 (3H, allylic CH$_3$), 2.49 (3H, allylic CH$_3$), 1.78 (m, 2H), 1.00 (t, 3H, J=7.5 Hz). $^{13}$C NMR (CDCl$_3$, 125 MHz) δ 161.82, 158.67, 147.68, 146.74, 135.16, 132.35, 125.33, 121.37, 121.03, 120.80, 113.68, 113.43, 86.10, 46.43, 23.07, 20.42, 18.07, 11.36. HRMS (ESI) calcd for C$_{18}$H$_{19}$N$_2$O$_3$ (M+H)$^+$: 311.1396, found: 311.1398. Melting Point: >250° C., 248-250° C. resulted in decomposition. IR (cm$^{-1}$): 1655 (s), 1623 (s), 1594 (m), 1556 (w), 1485 (w), 1439 (w), 1399 (w), 1352 (m), 1229 (w), 1154 (w).

Synthesized from bispinacolborane, (Z)-3-iodo-N-(4-methoxybenzyl)but-2-enamide, and (Z)-3-iodo-N-pentyl-but-2-enamide, by General Protocols A and B. 6% yield over 4 steps. Product is an off-white solid. $^1$H NMR (CDCl$_3$, 500 MHz) δ 7.47 (s, 1H, aryl CH), 6.54 (d, 1H, J=1.0 Hz, vinyl CH), 6.47 (d, 1H, J=1.0 Hz, vinyl CH), 6.40 (s, 2H, OCH$_2$N), 4.46 (m, 2H), 2.52 (d, 3H, J=1.0 Hz, allylic CH$_3$), 2.50 (d, 3H, J=1.0 Hz, allylic CH$_3$), 1.74 (pent, 2H, J=7.5 Hz), 1.38 (m, 4H), 0.91 (t, 3H, J=7.0 Hz). $^{13}$C NMR (CDCl$_3$, 125 MHz) δ 161.78, 158.67, 147.64, 146.64, 135.17, 132.37, 125.34, 121.38, 121.07, 120.83, 113.68, 113.43, 86.06, 45.06, 29.44, 29.11, 22.62, 20.35, 18.00, 14.22. HRMS (ESI-TOF) calcd for C$_{20}$H$_{23}$N$_2$O$_3$ (M+H)$^+$: 339.1709 found: 339.1704.

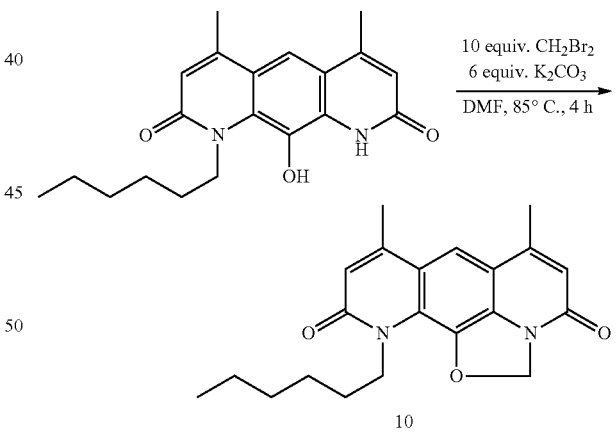

Synthesized from bispinacolborane, (Z)-3-iodo-N-(4-methoxybenzyl)but-2-enamide, and (Z)-N-hexyl-3-iodobut-2-enamide, by General Protocols A and B. 20% yield over 4 steps. Product is an off-white solid. $^1$H NMR (CDCl$_3$, 500 MHz) δ 7.47 (s, 1H, aryl CH), 6.52 (d, 1H, J=1.0 Hz, vinyl CH), 6.46 (d, 1H, J=1.0 Hz, vinyl CH), 6.39 (s, 2H, OCH$_2$N), 4.46 (m, 2H), 2.52 (d, 3H, J=1.0 Hz, allylic CH$_3$), 2.49 (d, 3H, J=1.0 Hz, allylic CH$_3$), 1.73 (pent, 2H, J=7.5 Hz), 1.42 (pent, 2H, J=7.5 Hz), 1.33 (m, 4H), 0.89 (t, 3H, J=7.0 Hz). HRMS (ESI-TOF) calcd for C$_{21}$H$_{25}$N$_2$O$_3$ (M+H)$^+$: 353.1865 found: 353.1870.

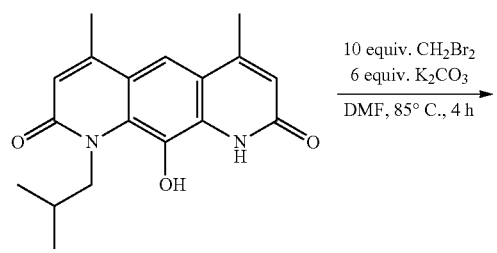

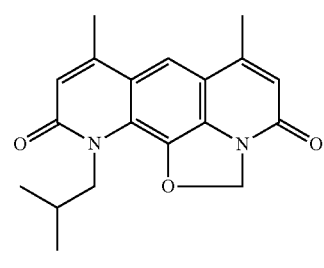

11

Synthesized from bispinacolborane, (Z)-3-iodo-N-(4-methoxybenzyl)but-2-enamide, and (Z)-3-iodo-N-isobutyl-but-2-enamide, by General Protocols A and B. 62% yield for methylene bridge insertion. 6% yield over 4 steps. Product is an off-white solid. $^1$H NMR (CDCl$_3$, 400 MHz) δ 7.47 (s, 1H, aryl CH), 6.52 (d, 1H, J=1.0 Hz, vinyl CH), 6.46 (d, 1H, J=1.0 Hz, vinyl CH), 6.39 (s, 2H, OCH$_2$N), 4.38 (d, 2H, J=7.2 Hz), 2.52 (d, 3H, J=1.0 Hz, allylic CH$_3$), 2.50 (d, 3H, J=1.0 Hz, allylic CH$_3$), 2.17 (sept, 1H, J=7.2 Hz), 0.95 (d, 1H, J=6.8 Hz). $^{13}$C NMR (CDCl$_3$, 125 MHz) δ 162.13, 158.65, 147.58, 146.51, 135.23, 132.38, 125.61, 121.34, 121.02, 120.81, 113.68, 113.40, 85.91, 50.88, 29.08, 20.33, 19.87, 17.96. HRMS (ESI-TOF) calcd for C$_{19}$H$_{21}$N$_2$O$_3$ (M+H)$^+$: 325.1552 found: 325.1553.

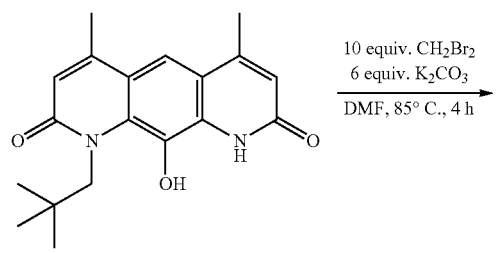

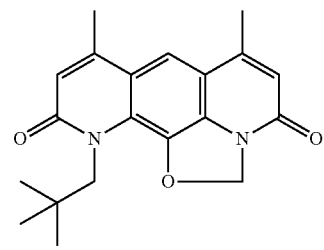

12

Synthesized from bispinacolborane, (Z)-3-iodo-N-(4-methoxybenzyl)but-2-enamide, and (Z)-3-iodo-N-neopen-tylbut-2-enamide, by General Protocols A and B. 30% yield over 4 steps. Product is an off-white solid. $^1$H NMR (CDCl$_3$, 500 MHz) δ 7.46 (s, 1H, aryl CH), 6.53 (d, 1H, J=1.0 Hz, vinyl CH), 6.45 (d, 1H, J=1.0 Hz, vinyl CH), 6.38 (s, 2H, OCH$_2$N), 4.56 (bs, 1H), 2.52 (d, 3H, J=1.0 Hz, allylic CH$_3$), 2.50 (d, 3H, J=1.0 Hz, allylic CH$_3$), 0.95 (s, 9H). $^{13}$C NMR (CDCl$_3$, 125 MHz) δ 162.91, 158.73, 147.68, 146.69, 135.45, 132.34, 126.92, 121.34, 121.08, 121.03, 113.69, 113.38, 85.69, 53.00, 35.34, 28.36, 20.42, 18.06. HRMS (ESI-TOF) calcd for C$_{20}$H$_{23}$N$_2$O$_3$ (M+H)$^+$: 339.1709 found: 339.1715. Melting Point: >200° C., 210-213° C. resulted in decomposition. IR (cm$^{-1}$): 1698 (w), 1658 (s), 1631 (s), 1606 (s), 1560 (w), 1474 (w), 1447 (w), 1353 (m), 1313 (w), 1258 (w), 1137 (m).

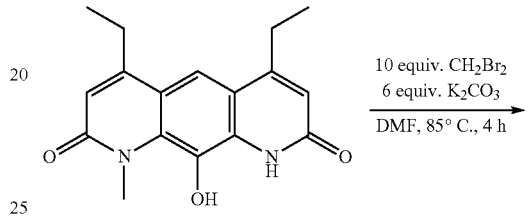

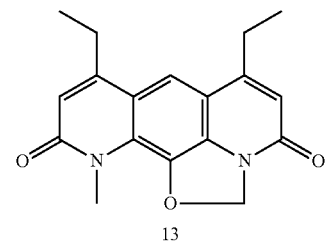

13

Synthesized from bispinacolborane, (Z)-3-iodo-N-(4-methoxybenzyl)pent-2-enamide, and ((Z)-3-iodo-N-methyl-pent-2-enamide, by General Protocols A and B. 7% yield over 4 steps. Product is an off-white solid. $^1$H NMR (CDCl$_3$, 500 MHz) δ 7.54 (s, 1H, aryl CH), 6.52 (1H, vinyl CH), 6.46 (1H, vinyl CH), 6.37 (s, 2H, OCH$_2$N), 3.92 (s, 3H, NCH$_3$), 2.88 (dq, 2H, J=1.0 Hz, 7.5 Hz), 2.87 (dq, 2H, J=1.0 Hz, 7.5 Hz), 1.36 (t, 3H, J=7.5 Hz), 1.34 (t, 3H, J=7.5 Hz). $^{13}$C NMR (CDCl$_3$, 125 MHz) δ 162.28, 158.87, 153.03, 151.86, 135.92, 132.32, 125.84, 119.93, 119.44, 118.39, 112.81, 112.49, 86.00, 32.60, 25.91, 24.52, 12.88. HRMS (ESI-TOF) calcd for C$_{18}$H$_{19}$N$_2$O$_3$ (M+H)$^+$: 311.1396 found: 311.1393. Melting Point: >200° C., 214-215° C. resulted in decomposition. IR (cm$^{-1}$): 1682 (w), 1657 (s), 1631 (s), 1595 (s), 1558 (w), 1455 (w), 1416 (m), 1370 (w), 1339 (m), 1261 (w), 1145 (w).

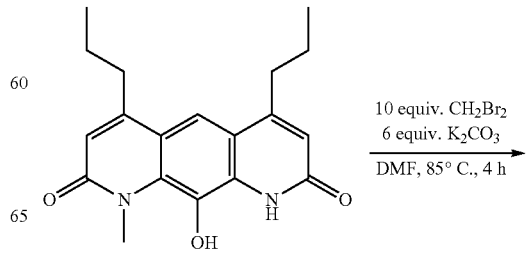

-continued

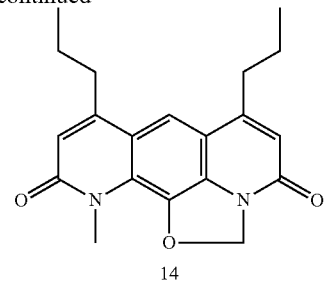

14

Synthesized from bispinacolborane, (Z)-3-iodo-N-(4-methoxybenzyl)hex-2-enamide, and (Z)-3-iodo-N-methyl-hex-2-enamide, by General Protocols A and B. 5% yield over 4 steps. Product is an off-white solid. $^1$H NMR (CDCl$_3$, 500 MHz) δ 7.53 (s, 1H, aryl CH), 6.51 (1H, vinyl CH), 6.45 (1H, vinyl CH), 6.38 (s, 2H, OCH$_2$N), 3.94 (s, 3H, NCH$_3$), 2.82 (t, 2H, J=7.5 Hz), 2.80 (t, 2H, J=7.5 Hz), 1.78 (m, 4H), 1.06 (t, 6H, J=7.5 Hz). $^{13}$C NMR (CDCl$_3$, 125 MHz) δ 161.96, 158.57, 151.44, 150.30, 135.78, 132.25, 125.76, 120.25, 119.75, 119.23, 112.79, 112.75, 85.92, 34.90, 33.29, 32.48, 21.91, 21.78, 14.07, 13.95. HRMS (ESI-TOF) calcd for C$_{20}$H$_{23}$N$_2$O$_3$ (M+H)$^+$: 339.1709 found: 339.1717. Melting Point: 171-173° C. IR (cm$^{-1}$): 1652 (s), 1627 (s), 1596 (s), 1556 (w), 1487 (w), 1458 (w), 1427 (m), 1378 (w), 1340 (m), 1326 (m), 1282 (w), 1143 (w).

10 equiv. CH$_2$Br$_2$
6 equiv. K$_2$CO$_3$
―――――→
DMF, 85° C., 4 h

15

Synthesized from bispinacolborane, (Z)-3-iodo-N-(4-methoxybenzyl)hex-2-enamide, and (Z)-N-butyl-3-iodo-hex-2-enamide by General Protocols A and B. 6% yield over 4 steps. Product is an off-white solid. $^1$H NMR (CDCl$_3$, 500 MHz) δ 7.56 (s, 1H, aryl CH), 6.53 (1H, vinyl CH), 6.46 (1H, vinyl CH), 6.40 (s, 2H, OCH$_2$N), 4.48 (m, 2H), 2.83 (t, 2H, J=7.5 Hz), 2.81 (t, 2H, J=7.5 Hz), 1.70-1.83 (m, 6H), 1.45 (sext, 2H, J=7.5 Hz), 1.07 (t, 3H, J=7.5 Hz), 1.06 (t, 3H, J=7.5 Hz), 0.97 (t, 3H, J=7.5 Hz). $^{13}$C NMR (CDCl$_3$, 125 MHz) δ 161.92, 158.77, 151.57, 150.33, 135.42, 132.38, 125.38, 120.36, 120.18, 119.60, 113.19, 112.81, 85.94, 44.88, 35.14, 33.46, 31.84, 22.10, 21.97, 20.21, 14.23, 14.08. HRMS (ESI-TOF) calcd for C$_{23}$H$_{29}$N$_2$O$_3$ (M+H)$^+$: 381.2178 found: 381.2167. Melting Point: 156-158° C. IR (cm$^{-1}$): 1658 (s), 1629 (s), 1596 (m), 1557 (w), 1485 (w), 1445 (w), 1422 (w), 1397 (w), 1336 (w), 1315 (w), 1271 (w), 1219 (w).

Example 2. Analysis of DNM and Derivatives

Bacterial Strains.

MRSA and *P. aeruginosa* isolates were from Cubist Pharmaceuticals. VRE isolates were from a previously published collection[50]. *E. coli* strains were obtained either from ATCC or Prof Cari Vanderpool (UIUC). *A. baumannii* isolates were obtained from Dr. John Quale[51].

Antibiotic Susceptibility Tests.

Susceptibility testing was performed in triplicate using the microdilution broth method as outlined by the Clinical and Laboratory Standards Institute CLSI[52]. MH broth was used.

DNA Amplification and Sequencing Analysis.

The *S. aureus* and *Enterococcus* DNA fragments containing the QRDR of gyrA and parC were amplified by PCR using Platinum TaqDNA Polymerase (Invitrogen). The primers are described in Table 7 (FIG. 15) DNA sequencing was performed by the W. M. Keck Center for Comparative and Functional Genomics (UIUC). The NCBI standard nucleotide BLAST database was used to verify the identity of the PCR products and determine mutations within the sequences.

Site Directed Mutagenesis.

pTRCHisA-GyrA plasmid containing the gene for *E. coli* gyrase A was kindly provided by Prof David Hooper[53]. Primers for mutagenesis were designed using QuikChange Primer Design (Agilent) and their sequences can be found in Table 7 (FIG. 15). Site directed mutagenesis was carried out with the QuikChange Lightning Site-Directed Mutagenesis Kit (Agilent) according to the manufacturer's instructions with the modification that NEB Turbo Competent *E. coli* were used as the host strain. All clones were confirmed by sequencing.

DNA Gyrase Expression.

Expression of WT *E. coli* gyrase A and gyrase B was performed as previously described[53]. Expression of S83L and S83R GyrA was performed identically to expression of the WT GyrA. Full details of the expression can be found in the Materials and Methods section below.

DNA Gyrase Cleavage.

DNA gyrase cleavage assays were performed as previously described with minor changes[12,37,54]. Details of the DNA gyrase cleavage can be found in the Materials and Methods section below.

Resistant Mutant Generation.

Agar plates (15 cm) were prepared containing MH broth and antibacterial compounds at concentrations detailed in the FIG. 10. 40 mL of an overnight bacterial culture was centrifuged at 3000×g for 10 min and resuspended in 0.4 mL of sterile PBS. Plates were inoculated with 100 μL of bacteria in PBS by spreading with beads. Inoculated plates were then incubated at 37° C. for 72 h and the number of resistant colonies was counted. To determine the number of viable colonies spread onto each plate, dilutions of the overnight culture in sterile PBS were spread onto nonselective MH agar plates and plates were incubated overnight at 37° C. before counting colonies.

In Vitro Hemolysis Assay.

Hemolysis assays were performed as previously described[55]. Details of the hemolysis assay can be found in the Materials and Methods section below.

Intercalation Assay.

Intercalation assays were performed as previously described[34]. Details of the intercalation assay can be found in the Materials and Methods section below.

Pharmacokinetic Assessment.

The animal studies (PK, in vivo toxicity and in vivo efficacy) were carried out in strict accordance with the recommendations in the Guide for the Care and Use of Laboratory Animals of the National Institutes of Health. The protocol was approved by the Institutional Animal Care and Use Committee (IACUC) at the University of Illinois at Urbana-Champaign (Protocol Number: 13406). In these studies, 10-12 week old female C57BL/6 mice purchased from Charles River were used. DNM, DNM-2, and DNM-3 were formulated as slurries at 8.3 mg mL$^{-1}$ in 25% Cremophor RH40/water (v/v). Before beginning the pharmacokinetic assessment, mice were first tested for their ability to tolerate the DNM, DNM-2, and DNM-3 at 50 mg kg$^{-1}$ (p.o.). After establishing that this dose was well tolerated, mice were treated with DNM, DNM-2, or DNM-3 (all 50 mg kg$^{-1}$) via oral gavage with 3 mice per time point (15, 30, 60, 120, 240, and 480 min). At specified time points, mice were sacrificed and blood was collected, centrifuged, and the serum was frozen at −80° C. until analysis. The proteins in a 50 μL aliquot of serum were precipitated by the addition of 50 μL of acetonitrile and the sample was centrifuged to remove the proteins. Serum concentrations of DNM, DNM-2, and DNM-3 were determined by HPLC. PK parameters were determined using GraphPad Prism Version 5.00 for Windows.

In Vivo Toxicity Assessment.

The protocol was approved by the Institutional Animal Care and Use Committee (IACUC) at the University of Illinois at Urbana-Champaign (Protocol Number: 14032). Six-week old male pathogen-free BALB/c mice were purchased from Taconics Biosciences (Albany, N.Y.). All animals were housed in a pathogen free environment and received sterile food and water. Mice (n=5) were treated once daily for 10 days with 50 mg kg$^{-1}$ DNM-2 or vehicle (25% Cremophor RH 40/PBS (v/v)) by oral gavage. Toxicity was assessed as previously described[56]. Specifically, heparinized whole blood was collected for assessment of total white blood cells, neutrophils, lymphocytes, hematocrit, platelets, creatinine, blood urea, nitrogen, albumin, alanine aminotransferase, alkaline phosphatase, and total bilirubin. Mice were euthanized by overdosing with Ketamine/Xylazine, and heart, lung, kidney, liver, spleen, gastrointestinal tract and brain were collected for histopathology. Tissue samples were fixed 24 hours in 10% neutral buffered formalin, processed, and paraffin embedded, sectioned (5 μm thickness) and stained with hematoxylin and eosin. All slides were systematically evaluated by a single board certified veterinary anatomic pathologist (SL) for evidence of acute or chronic inflammation and toxicity. All lesions were characterized, recorded, and scored for severity (minimal=1, mild=2, moderate=3, and severe=4).

In Vivo Efficacy.

The protocol was approved by the Institutional Animal Care and Use Committee (IACUC) at the University of Illinois at Urbana-Champaign (Protocol Number: 14032). Six-week old male pathogen-free BALB/c mice were purchased from Harlan Sprague-Dawley (Indianapolis, Ind.). All animals were housed in a pathogen free environment and received sterile food and water. For the inoculation, overnight cultures of S. aureus clinical isolate NRS3 were diluted 1:100 into fresh tryptic soy broth (TSB) and grown for 2 h at 37° C. Bacteria were washed and resuspended in sterile PBS. The mice were anesthetized with ketamine and xylazine. The mouse tails were pre-warmed in 45° C. for 5 minutes before 1.2×10$^8$ CFU of S. aureus in 50 μL of PBS were injected into a tail vein using a 29-gauge needle. This number of bacteria was determined from a series of preliminary studies in which groups of mice were infected with a range of 10$^6$ to 10$^9$ CFU of S. aureus. Infected mice (15 mice per group) were then treated once daily for 10 days with 50 mg kg$^{-1}$ DNM-2, 50 mg kg$^{-1}$ CIP, or vehicle (25% Cremophor RH 40/PBS (v/v)) by oral gavage. For survival analyses a Kaplan-Meier Log Rank Survival Test was performed using OriginPro 9 (Northampton, Mass.).

Materials and Methods.

DNA Amplification and Sequencing Analysis.

Briefly, a single colony of S. aureus grown on MH agar or a single colony of Enterococcus grown on BHI agar was suspended in 50 μL of the PCR mixture containing the primers (Table 4) and PCR master mix (Platinum TaqDNA Polymerase, invitrogen). PCR amplification was performed using an initial denaturation step of 94° C. for 2 minutes followed by 35 cycles of 94° C. for 30 s, 52° C. (S. aureus. or Enterococcus faecalis) or 58° C. (Enterccocus faecium) for 30 s, 72° C. for 50 s. PCR products were purified further on a 1% agarose gel and DNA was extracted (QIAquick Gel Extraction Kit, Qiagen). DNA sequencing was performed by the W. M. Keck Center for Comparative and Functional Genomics (UIUC). The NCBI standard nucleotide BLAST database was used to verify the identity of the PCR products and determine mutations within the sequences.

DNA Gyrase Expression.

Briefly, pTRCHisA-GyrA, pTRCHisA-GyrAS83L, pTRCHisA-GyrAS83R, or pTRCHisA-GyrB were introduced into One Shot BL21 Star (DE3) (NEB) by chemical transformation. Transformed cells were selected for on an LB ampicillin plate. Single colonies from a fresh plate were inoculated into 50 mL of LB with 50 μg/mL ampicillin and incubated aerobically at 37° C. with shaking at 250 rpm overnight (14-16 h). The overnight culture was then used to inoculate 1 L LB with 50 μg/mL ampicillin. The culture was grown aerobically with shaking at 250 rpm until A600 reached 0.4-0.6. Protein expression was induced with a final concentration of 0.5 mM of IPTG at 37° C. with shaking at 250 rpm for 4 h. The culture was harvested by centrifugation at 5000×g for 5 min at 4° C. Cell pellets were frozen at −20° C., thawed on ice for 30 min, and resuspended in TGN$_{150}$ (20 mM Tris-HCl [pH 7.5], 10% glycerol, 150 mM NaCl) with 0.5 mg/mL lysozyme with 2 μg/mL aprotinin, 1 μg/mL leupeptin, 1 μg/mL pepstatin A, and 100 μM phenylmethanesulfonylfluoride. Cells were lysed by sonication at 35% amplitude (10 s pulse with 30 s rest, 6 times). The lysate was cleared by centrifugation at 35,000×g for 30 min at 4° C. The supernatant was batch-loaded onto 1 mL of 1:1 Ni-NTA agarose (Qiagen) at 4° C. for 30 min with inversion. The resin was washed with 20 mL TGN$_{150}$ with 10 mM imidazole followed by 10 mL of wash buffer (20 mM Tris-HCl (pH 7.5), 10% glycerol, 300 mM NaCl, 10 mM imidazole) and eluted with TGN150 containing imidazole concentrations of 25, 50, 100, 200, 300, and 500 mM. Eluted fractions were assessed by sodium dodecyl sulfate-polyacrylamide gel electrophoresis (SDS-PAGE) using 4-20% TGX Mini-PROTEAN gels (Bio-Rad). Fractions containing pure protein were pooled and dialyzed against TDEN buffer (50 mM Tris-HCl [pH 7.5], 5 mM dithiothreitol, 1 mM EDTA, 150 mM NaCl) overnight at 4° C. utilizing a Slide-A-Lyzer Dialysis Cassette, 10 000 MWCO (Thermo Scientific) and concentrated to ~0.5-1 mL using an Amicon Ultra-15 50K Centrifugal Filter Device. The concentration was determined by Bradford assay (Sigma) using bovine serum albumin (BSA, Thermo Scientific) as the control.

DNA Gyrase Cleavage Assays.

For cleavage assays, 10 µg/mL supercoiled DNA (pBR322, Inspiralis) was added to buffer (35 mM TrisHCl pH 7.5, 24 mM KCl, 4 mM $MgCl_2$, 2 mM DTT, 1.8 mM spermidine, 6.5% glycerol, 0.1 mg/mL albumin) with compound or vehicle. Compound concentrations were 0.01, 0.04, 0.17, 0.68, 2.7, and 10.8 µM except for DNM which was 8.9 µM for its highest concentration. DNA gyrase was added to a final concentration of 16 nM gyrA and 32 nM gyrA (giving a final concentration of A2B2 of 8 nM) for 25 min at 30° C. Linear product was revealed by addition of 0.2% SDS and 0.1 µg/mL proteinase K for 30 min at 37° C. DNA loading dye (Thermo Scientific) was added to the samples and they were run on 1% agarose gels containing 0.5 µg/mL ethidium bromide. Gels were imaged on a Molecular Imager Gel Doc XR+ (Biorad) and bands were quantified using ImageJ (Schneider et al., Nat Methods 9, 671-675, (2012)). Percent of type of DNA was calculated with total DNA in each lane being 100%. For time-course cleavage assays, the same protocol was followed except that the initial incubation was for varying times (0, 1, 3, 5, 10, 15, 20, 30, 60, 90, 120, and 180 min) instead of 25 min.

Human Topoisomerase Decatenation Assay.

The decatenation assay was performed with the Human Topo II Decatenation Assay Kit (Inspiralis) according to the manufacturer's instructions with minor modifications. First, a master mix was made containing 2 µL 10× assay buffer (500 mM Tris.HCl, pH 7.5, 1250 mM NaCl, 100 mM $MgCl_2$, 50 mM DTT, 1000 µg/mL albumin), 0.67 µL 30 mM ATP, 1.34 µL 0.1 ng/µL kDNA, and 14.3 µL of nuclease free water per sample is made. DMSO or 30× compound is added to a 0.5 mL Eppendorf tube (0.67 µL per tube). The master mix is then added to each tube (18.3 µL per tube). Finally, 1 U of human topoisomerase (1 µL of 1 U/µL stock) is added to each tube for a final volume of 20 µL. The tubes are then incubated at 37° C. for 30 min. Reactions are stopped by the addition of 20 µL of 24:1 chloroform:isoamyl alcohol and 20 µL of stop dye (40% sucrose, 1 mM EDTA, 100 mM TrisHCl pH 7.5, 0.5 µg/mL bromophenol blue). Samples were run on 1% agarose gels containing 0.5 µg/mL ethidium bromide for 1 h at 110V or until the dye front was approximately halfway down the gel. Gels were imaged on a Molecular Imager Gel Doc XR+ (Biorad).

In Vitro Hemolysis Assay.

Briefly, assays were performed using human erythrocytes within three days of receipt. One milliliter of human blood purchased from Bioreclamation, Inc. (Hicksville, N.Y.) was centrifuged (10 000×g, 2 min) The pellet was washed three times with sterile saline (0.9% NaCl in water) by repeated gentle suspension and centrifugation. The pellet was resuspended in red blood cell (RBC) buffer (10 mM $Na_2HPO_4$, 150 mM NaCl, 1 mM $MgCl_2$, pH 7.4). To evaluate hemolytic activity of DNM and derivatives, 1 µL either 3.2 mg/mL DMSO stock (or the most concentrated stock of the compound available if not soluble at 3.2 mg/mL in DMSO) was transferred to 0.5 mL Eppendorf tubes containing 19 µL RBC buffer. Negative control tubes contained 1 µL DMSO and 19 µL RBC buffer and positive control tubes contained 1 µL DMSO and 19 µL sterile deionized water. A suspension of washed erythrocytes (10 µL) was added to each tubes and samples were incubated at 37° C. for 2 h. Samples were centrifuged at 10,000×g for 2 min and the supernatants from each sample (25 µL) were transferred to a clear, sterile 384-well plate. The absorbance of these supernatants was measured at 540 nm using a SpectraMaxPlus384 absorbance plate reader (Molecular Devices). Percent hemolysis of each sample was calculated relative to the average absorbance values measured for positive controls.

Intercalation Assay.

These assays were performed as previously described (Bair et al. J. Am. Chem. Soc. 132, 5469-5478, (2010)). The ability of DNM-2 to intercalate into DNA was measured by an ethidium bromide displacement assay. Herring Sperm DNA (34 µg/mL final) was premixed with buffer containing ethidium bromide (50 mM Tris base, 100 mM NaCl, 1 mM EDTA, 5 µM EtBr, pH=7.5). 95 µL of this solution was added to a 96 well plate containing 5 µL of DMSO solutions of compounds. In addition to vehicle controls, wells lacking either DNA or EtBr were also used to ensure that these did not have an effect on fluorescence. Doxorubicin was used as a positive control. The reactions were allowed to incubate for 30 minutes. Fluorescence was then read on a Gemini microplate reader (Molecular Devices, excitation=545 nm, emission=595 nm).

Aqueous Solubility Determination.

Initially a small amount of solid compound (generally 0.5 to 1.5 mg) was measured into a 1.7 mL Eppendorf tube. Phosphate buffered saline (pH 7.4) was added to give a maximum final concentration of 1 mg/mL of compound. The compound was vortexed for ~30 seconds before being placed into a bath sonicator (Cole Parmer, ultrasonic cleaner) for 1 h. Longer incubation times (up to 24 h) were performed with select compounds and no difference in solubility was observed so 1 h was used for all subsequent testing. The tubes were vortexed again for 30 s before being centrifuged at maximum speed (13,000×g) for 10 minutes. The supernatant was then filtered through a 0.22 µm syringe filter (Millipore Millex MP). The filtrate was then analyzed by LC-MS (λ=254 nm, ESI-TOF in positive mode, Agilent Technologies 6230 TOF LC/MS). The filtrate was diluted 1:2 and 1:4 and all three samples (1×, 0.5× and 0.25×) were analyzed in triplicate. Three independent replicates of each compound were performed. A calibration curve for each compound was generated from 1-400 µM by dissolving the compound in DMSO and making dilutions of the stock in DMSO. The calibration curve (measured by UV absorbance) was linear over this range. The concentration of the samples was calculated based on the calibration curves.

CITATIONS

1 Hooper, D. C. Fluoroquinolone resistance among Gram-positive cocci. Lancet Infect. Dis. 2, 530-538, (2002).
2 Linder, J. A., Huang, E. S., Steinman, M. A., Gonzales, R. & Stafford, R. S. Fluoroquinolone prescribing in the United States: 1995 to 2002. Am J Med 118, 259-268, (2005).
3 Hicks, L. A., Taylor, T. H., Jr. & Hunkler, R. J. U.S. outpatient antibiotic prescribing, 2010. N Engl J Med 368, 1461-1462, (2013).
4 Redgrave, L. S., Sutton, S. B., Webber, M. A. & Piddock, L. J. Fluoroquinolone resistance: mechanisms, impact on bacteria, and role in evolutionary success. Trends Microbiol. 22, 438-445, (2014).
5 Chambers, H. F. in Basic and Clinical Pharmacology (ed B. G. Katzung) Ch. 46, 763-770 (McGraw-Hill 2007).

6 Chen, S. H., Chan, N. L. & Hsieh, T. S. New mechanistic and functional insights into DNA topoisomerases. *Annu. Rev. Biochem.* 82, 139-170, (2013).

7 Pommier, Y. Drugging topoisomerases: lessons and challenges. *ACS Chem Biol* 8, 82-95, (2013).

8 Gellert, M., Mizuuchi, K., O'Dea, M. H. & Nash, H. A. DNA gyrase: an enzyme that introduces superhelical turns into DNA. *Proc. Natl. Acad. Sci. USA* 73, 3872-3876, (1976).

9 Jacoby, G. A. Mechanisms of resistance to quinolones. *Clin Infect Dis* 41 Suppl 2, S120-126, (2005).

10 Dalhoff, A. Resistance surveillance studies: a multifaceted problem—the fluoroquinolone example. *Infection* 40, 239-262, (2012).

11 Aldred, K. J., Schwanz, H. A., Li, G., McPherson, S. A., Turnbough, C. L., Jr., Kerns, R. J. & Osheroff, N. Overcoming target-mediated quinolone resistance in topoisomerase IV by introducing metal-ion-independent drug-enzyme interactions. *ACS Chem Biol* 8, 2660-2668, (2013).

12 Barnard, F. M. & Maxwell, A. Interaction between DNA gyrase and quinolones: effects of alanine mutations at GyrA subunit residues Ser(83) and Asp(87). *Antimicrob Agents Chemother* 45, 1994-2000, (2001).

13 Kwak, Y. G., Truong-Bolduc, Q. C., Bin Kim, H., Song, K. H., Kim, E. S. & Hooper, D. C. Association of norB overexpression and fluoroquinolone resistance in clinical isolates of *Staphylococcus aureus* from Korea. *J Antimicrob Chemother* 68, 2766-2772, (2013).

14 Wang, S., Wang, Y., Shen, J., Wu, Y. & Wu, C. Polymorphic mutation frequencies in clinical isolates of *Staphylococcus aureus*: the role of weak mutators in the development of fluoroquinolone resistance. *FEMS Microbiol Lett* 341, 13-17, (2013).

15 Hiramatsu, K., Igarashi, M., Morimoto, Y., Baba, T., Umekita, M. & Akamatsu, Y. Curing bacteria of antibiotic resistance: reverse antibiotics, a novel class of antibiotics in nature. *Int J Antimicrob Agents* 39, 478-485, (2012).

16 Baba, K., Ishihara, K., Ozawa, M., Usui, M., Hiki, M., Tamura, Y. & Asai, T. Prevalence and mechanism of antimicrobial resistance in *Staphylococcus aureus* isolates from diseased cattle, swine and chickens in Japan. *J Vet Med Sci* 74, 561-565, (2012).

17 Costa, S. S., Falcao, C., Viveiros, M., Machado, D., Martins, M., Melo-Cristino, J., Amaral, L. & Couto, I. Exploring the contribution of efflux on the resistance to fluoroquinolones in clinical isolates of *Staphylococcus aureus*. *BMC Microbiol* 11, 241, (2011).

18 Sanfilippo, C. M., Hesje, C. K., Haas, W. & Morris, T. W. Topoisomerase mutations that are associated with high-level resistance to earlier fluoroquinolones in *Staphylococcus aureus* have less effect on the antibacterial activity of besifloxacin. *Chemotherapy* 57, 363-371, (2011).

19 Aligholi, M., Mirsalehian, A., Halimi, S., Imaneini, H., Taherikalani, M., Jabalameli, F., Asadollahi, P., Mohajer, B., Abdollahi, A. & Emaneini, M. Phenotypic and genotypic evaluation of fluoroquinolone resistance in clinical isolates of *Staphylococcus aureus* in Tehran. *Med Sci Monit* 17, PH71-74, (2011).

20 Yoon, E. J., Lee, C. Y., Shim, M. J., Min, Y. H., Kwon, A. R., Lee, J. & Choi, E. C. Extended spectrum of quinolone resistance, even to a potential latter third-generation agent, as a result of a minimum of two Gr1A and two GyrA alterations in quinolone-resistant *Staphylococcus aureus*. *Chemotherapy* 56, 153-157, (2010).

21 Coskun-Ari, F. F. & Bosgelmez-Tinaz, G. grlA and gyrA mutations and antimicrobial susceptibility in clinical isolates of ciprofloxacin-methicillin-resistant *Staphylococcus aureus*. *Eur J Med Res* 13, 366-370, (2008).

22 Sadowy, E., Sienko, A., Gawryszewska, I., Bojarska, A., Malinowska, K. & Hryniewicz, W. High abundance and diversity of antimicrobial resistance determinants among early vancomycin-resistant Enterococcus faecium in Poland. *Eur J Clin Microbiol Infect Dis* 32, 1193-1203, (2013).

23 Werner, G., Fleige, C., Ewert, B., Laverde-Gomez, J. A., Klare, I. & Witte, W. High-level ciprofloxacin resistance among hospital-adapted Enterococcus faecium (CC17). *Int J Antimicrob Agents* 35, 119-125, (2010).

24 Grohs, P., Houssaye, S., Aubert, A., Gutmann, L. & Varon, E. In vitro activities of garenoxacin (BMS-284756) against *Streptococcus pneumoniae*, viridans group streptococci, and *Enterococcus faecalis* compared to those of six other quinolones. *Antimicrob Agents Chemother* 47, 3542-3547, (2003).

25 Tremblay, C. L., Charlebois, A., Masson, L. & Archambault, M. Characterization of hospital-associated lineages of ampicillin-resistant *Enterococcus faecium* from clinical cases in dogs and humans. *Front Microbiol* 4, 245, (2013).

26 Rathnayake, I. U., Hargreaves, M. & Huygens, F. Antibiotic resistance and virulence traits in clinical and environmental *Enterococcus faecalis* and *Enterococcus faecium* isolates. *Syst Appl Microbiol* 35, 326-333, (2012).

27 Brock, T. D. & Sokolski, W. T. Biological studies on the antibiotic, nybomycin. *Antibiot Chemother* (Northfield Ill) 8, 631-636, (1958).

28 Strelitz, F., Flon, H. & Asheshov, I. N. Nybomycin, A New Antibiotic with Antiphage and Antibacterial Properties. *Proc. Natl. Acad. Sci. U.S.A.* 41, 620-624, (1955).

29 Rinehart, K. L. & Renfroe, H. B. The Structure of Nybomycin. *J. Am. Chem. Soc.* 83, 3729-3731, (1961).

30 Naganawa, H. W., T.; Yagi, A.; Kondo, S.; Takita, T.; Hamada, M.; Maeda, K.; Umezawa, H. Deoxynybomycin from a Streptomyces. *J. Antibiot.* 23, 365-378, (1970).

31 Adelmann, S., Baldhoff, T., Koepcke, B. & Schembecker, G. Selection of operating parameters on the basis of hydrodynamics in centrifugal partition chromatography for the purification of nybomycin derivatives. *J Chromatogr A* 1274, 54-64, (2013).

32 Forbis, R. M. & Rinehart, K. L. Nybomycin .4. Total Synthesis of Deoxynybomycin. *J. Am. Chem. Soc.* 92, 6995-&, (1970).

33 Forbis, R. M. & Rinehart, K. L. Nybomycin .7. Preparative Routes to Nybomycin and Deoxynybomycin. *J. Am. Chem. Soc.* 95, 5003-5013, (1973).

34 Bair, J. S., Palchaudhuri, R. & Hergenrother, P. J. Chemistry and biology of deoxynyboquinone, a potent inducer of cancer cell death. *J. Am. Chem. Soc.* 132, 5469-5478, (2010).

35 Angibaud, P., Bourdrez, X., Devine, A., End, D. W., Freyne, E., Ligny, Y., Muller, P., Mannens, G., Pilatte, I., Poncelet, V., Skrzat, S., Smets, G., Van Dun, J., Van Remoortere, P., Venet, M. & Wouters, W. 5-imidazolyl-quinolinones, -quinazolinones and -benzo-azepinones as farnesyltransferase inhibitors. *Bioorg. Med. Chem. Lett.* 13, 1543-1547, (2003).

36 Parkinson, E. I., Bair, J. S., Cismesia, M. & Hergenrother, P. J. Efficient NQO1 substrates are potent and selective anticancer agents. *ACS Chem Biol* 8, 2173-2183, (2013).

37 Kampranis, S. C. & Maxwell, A. The DNA gyrase-quinolone complex. ATP hydrolysis and the mechanism of DNA cleavage. *J Biol Chem* 273, 22615-22626, (1998).

38 Bax, B. D., Chan, P. F., Eggleston, D. S., Fosberry, A., Gentry, D. R., Gorrec, F., Giordano, I., Hann, M. M., Hennessy, A., Hibbs, M., Huang, J., Jones, E., Jones, J., Brown, K. K., Lewis, C. J., May, E. W., Saunders, M. R., Singh, O., Spitzfaden, C. E., Shen, C., Shillings, A., Theobald, A. J., Wohlkonig, A., Pearson, N. D. & Gwynn, M. N. Type IIA topoisomerase inhibition by a new class of antibacterial agents. *Nature* 466, 935-940, (2010).

39 Ferrero, L., Cameron, B. & Crouzet, J. Analysis of gyrA and grlA mutations in stepwise-selected ciprofloxacin-resistant mutants of *Staphylococcus aureus*. *Antimicrob Agents Chemother* 39, 1554-1558, (1995).

40 Hori, S., Ohshita, Y., Utsui, Y. & Hiramatsu, K. Sequential acquisition of norfloxacin and ofloxacin resistance by methicillin-resistant and -susceptible *Staphylococcus aureus*. *Antimicrob Agents Chemother* 37, 2278-2284, (1993).

41 Egawa K, Y. T., Nosaka C, Kunimoto S, Takeuchi T, Nos K. Deoxynybomycin is a selective anti-tumor agent inducing apoptosis and inhibiting topoisomerase I. *Biol. Pharm. Bull.* 23, 1036-1040, (2000).

42 Li, S., Tian, X., Niu, S., Zhang, W., Chen, Y., Zhang, H., Yang, X., Li, W., Zhang, S., Ju, J. & Zhang, C. Pseudonocardians A-C, new diazaanthraquinone derivatives from a deap-sea actinomycete *Pseudonocardia* sp. SCSIO 01299. *Mar Drugs* 9, 1428-1439, (2011).

43 Price, L. B., Vogler, A., Pearson, T., Busch, J. D., Schupp, J. M. & Keim, P. In vitro selection and characterization of *Bacillus anthracis* mutants with high-level resistance to ciprofloxacin. *Antimicrob Agents Chemother* 47, 2362-2365, (2003).

44 Vila et al., Association between double mutation in gyrA gene of ciprofloxacin-resistant clinical isolates of *Escherichia coli* and MICs. *Antimicrob Agents Chemother* 38, 2477-2479, (1994).

45 Vila, J., Ruiz, J., Goni, P., Marcos, A. & Jimenez de Anta, T. Mutation in the gyrA gene of quinolone-resistant clinical isolates of *Acinetobacter baumannii*. *Antimicrob Agents Chemother* 39, 1201-1203, (1995).

46 Vernel-Pauillac, F., Hogan, T. R., Tapsall, J. W. & Goarant, C. Quinolone resistance in Neisseria gonorrhoeae: rapid genotyping of quinolone resistance-determining regions in gyrA and parC genes by melting curve analysis predicts susceptibility. *Antimicrob Agents Chemother* 53, 1264-1267, (2009).

47 Deguchi et al., Alterations in the GyrA subunit of DNA gyrase and the ParC subunit of topoisomerase IV in quinolone-resistant clinical isolates of *Klebsiella pneumoniae*. *Antimicrob Agents Chemother* 41, 699-701, (1997).

48 Bast, D. J., Low, D. E., Duncan, C. L., Kilburn, L., Mandell, L. A., Davidson, R. J. & de Azavedo, J. C. Fluoroquinolone resistance in clinical isolates of Streptococcus pneumoniae: contributions of type II topoisomerase mutations and efflux to levels of resistance. *Antimicrob Agents Chemother* 44, 3049-3054, (2000).

49 Talbot, G. H., Bradley, J., Edwards, J. E., Jr., Gilbert, D., Scheld, M. & Bartlett, J. G. Bad bugs need drugs: an update on the development pipeline from the Antimicrobial Availability Task Force of the Infectious Diseases Society of America. *Clin Infect Dis* 42, 657-668, (2006).

50 Moritz, E. M. & Hergenrother, P. J. Toxin-antitoxin systems are ubiquitous and plasmid-encoded in vancomycin-resistant enterococci. *Proc. Natl. Acad. Sci. USA* 104, 311-316, (2007).

51 Bratu, S., Landman, D., Martin, D. A., Georgescu, C. & Quale, J. Correlation of antimicrobial resistance with beta-lactamases, the OmpA-like porin, and efflux pumps in clinical isolates of Acinetobacter baumannii endemic to New York City. *Antimicrob Agents Chemother* 52, 2999-3005, (2008).

52 Wikler et al., *Methods for dilution antimicrobial susceptibility tests for bacteria that grow aerobically; approved standard*. 7 edn, Vol. 26 (Clinical and Laboratory Standards Institute, 2006).

53 Tran, J. H., Jacoby, G. A. & Hooper, D. C. Interaction of the plasmid-encoded quinolone resistance protein Qnr with *Escherichia coli* DNA gyrase. *Antimicrob Agents Chemother* 49, 118-125, (2005).

54 Fisher, L. M. & Pan, X. S. Methods to assay inhibitors of DNA gyrase and topoisomerase IV activities. *Methods Mol Med* 142, 11-23, (2008).

55 Eibergen, N. R., Im, I., Patel, N. Y. & Hergenrother, P. J. Identification of a novel protein synthesis inhibitor active against gram-positive bacteria. *Chembiochem* 13, 574-583, 490, (2012).

56 Botham, R. C., Fan, T. M., Im, I., Borst, L. B., Dirikolu, L. & Hergenrother, P. J. Dual small-molecule targeting of procaspase-3 dramatically enhances zymogen activation and anticancer activity. *J. Am. Chem. Soc.* 136, 1312-1319, (2014).

Example 2. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |

-continued

| (x) Topical Cream 1 | wt. % |
|---|---|
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

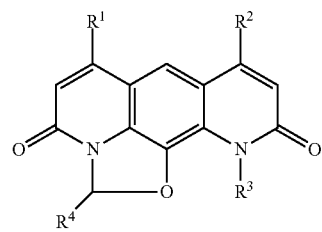

(I)

wherein $R^1$ is $(C_1-C_{12})$alkyl, $(C_1-C_{12})$alkyl$(C_3-C_{12})$cycloalkyl, or $(C_3-C_{12})$cycloalkyl, where alkyl can be straight or branched;

$R^2$ is $(C_1-C_{12})$alkyl, $(C_1-C_{12})$alkyl$(C_3-C_{12})$cycloalkyl, or $(C_3-C_{12})$cycloalkyl, where alkyl can be straight or branched;

$R^3$ is $(C_1-C_{12})$alkyl, $(C_1-C_{12})$alkyl$(C_3-C_{12})$cycloalkyl, or $(C_3-C_{12})$cycloalkyl, where alkyl can be straight or branched; and $R^4$ is H, $(C_1-C_{12})$alkyl, $(C_1-C_{12})$alkyl$(C_3-C_{12})$cycloalkyl, or $(C_3-C_{12})$cycloalkyl, where alkyl can be straight or branched;

provided that when $R^4$ is H, $R^1$, $R^2$, and $R^3$ are not each methyl.

2. The compound of claim 1 wherein $R^1$ is methyl, ethyl, or propyl.

3. The compound of claim 1 wherein $R^2$ is methyl, ethyl, or propyl.

4. The compound of claim 1 wherein $R^3$ is methyl, ethyl, propyl, butyl, iso-butyl, pentyl, neo-pentyl, or hexyl.

5. The compound of claim 1 wherein $R^4$ is H or methyl.

6. The compound of claim 1 wherein $R^1$ is methyl or ethyl; $R^2$ is methyl, ethyl, or propyl; $R^3$ is methyl, ethyl, propyl, or butyl; and $R^4$ is H or methyl.

7. The compound of claim 1 that is active against fluoroquinolone resistant bacteria with an MIC of less than 4 µg mL$^{-1}$.

8. The compound of claim 1 that is active against fluoroquinolone resistant bacteria with an MIC of less than 0.3 µg mL$^{-1}$.

9. The compound of claim 1 selected from compounds 2-15:

2
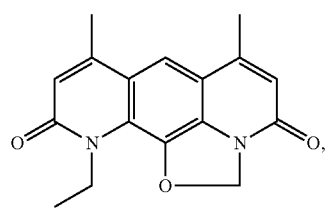
DNM-2

3
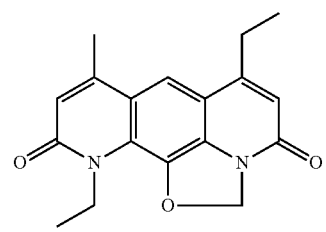

4
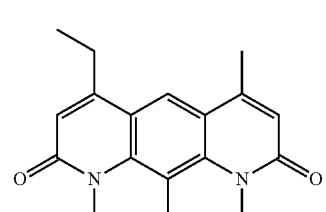

5
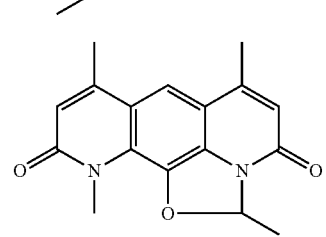

6
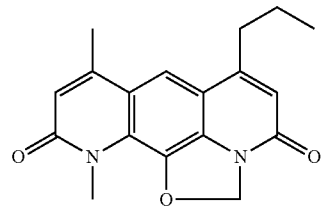

7
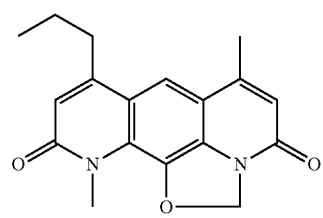

8
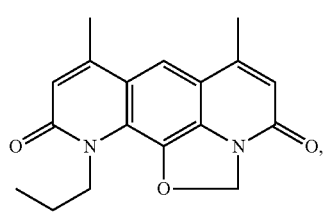
DNM-8

9
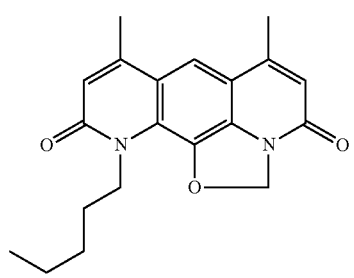

10
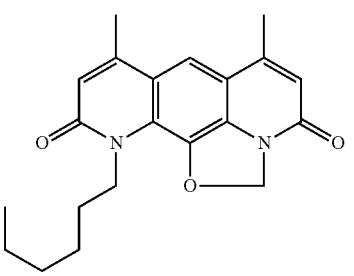

11
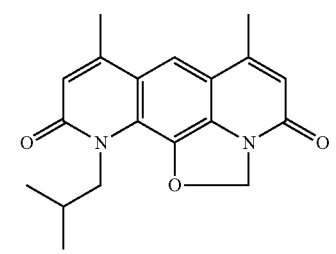

-continued

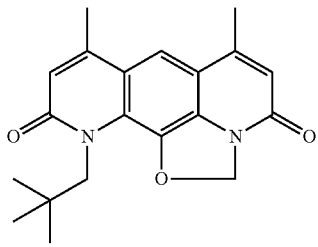
12

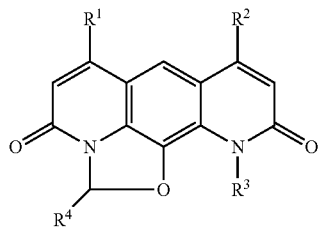
(II)

wherein
R¹ is $(C_1-C_{12})$alkyl, $(C_1-C_{12})$alkyl$(C_3-C_{12})$cycloalkyl, or $(C_3-C_{12})$cycloalkyl, where alkyl can be straight or branched;

R² is $(C_1-C_{12})$alkyl, $(C_1-C_{12})$alkyl$(C_3-C_{12})$cycloalkyl, or $(C_3-C_{12})$cycloalkyl, where alkyl can be straight or branched;

R³ is $(C_1-C_{12})$alkyl, $(C_1-C_{12})$alkyl$(C_3-C_{12})$cycloalkyl, or $(C_3-C_{12})$cycloalkyl, where alkyl can be straight or branched; and R⁴ is H, $(C_1-C_{12})$alkyl, $(C_1-C_{12})$alkyl$(C_3-C_{12})$cycloalkyl, or $(C_3-C_{12})$cycloalkyl, where alkyl can be straight or branched; provided that when R⁴ is H, R¹, R², and R³ are not each methyl;

in combination with the administration of an effective antibacterial amount of a fluoroquinolone antibiotic, thereby killing or inhibiting the growth of the fluoroquinolone-resistant bacteria and treating the infection.

13

14

15

15. The method of claim 14 wherein the fluoroquinolone-resistant bacteria are gram positive bacteria.

16. The method of claim 14 wherein the infection is caused methicillin-resistant *Staphylococcus aureus* (MRSA) or vancomycin-resistant enterococci (VRE).

17. A method of making a compound of Formula I:

10. A pharmaceutical composition comprising a compound claim 1 in combination with a pharmaceutically acceptable diluent, excipient, or carrier.

11. A method of killing or inhibiting the growth of a bacteria comprising contacting a bacteria with an effective antibacterial amount of a compound of claim 1.

12. The method of claim 11 wherein the bacteria is methicillin-resistant *Staphylococcus aureus* (MRSA) or vancomycin-resistant enterococci (VRE).

13. A method of treating a bacterial infection in a subject comprising administering to a subject having a bacterial infection an effective amount of a compound of claim 1.

14. A method of treating an infection caused by fluoroquinolone-resistant bacteria comprising administering to a mammal in need of such treatment an effective antibacterial amount of a compound of Formula II:

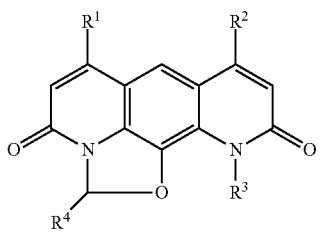
(I)

wherein
R¹ is $(C_1-C_{12})$alkyl, $(C_1-C_{12})$alkyl$(C_3-C_{12})$cycloalkyl, or $(C_3-C_{12})$cycloalkyl, where alkyl can be straight or branched;

R² is $(C_1-C_{12})$alkyl, $(C_1-C_{12})$alkyl$(C_3-C_{12})$cycloalkyl, or $(C_3-C_{12})$cycloalkyl, where alkyl can be straight or branched;

R³ is $(C_1-C_{12})$alkyl, $(C_1-C_{12})$alkyl$(C_3-C_{12})$cycloalkyl, or $(C_3-C_{12})$cycloalkyl, where alkyl can be straight or branched; and $R^4$ is H, $(C_1-C_{12})$alkyl, $(C_1-C_{12})$alkyl$(C_3-C_{12})$cycloalkyl, or $(C_3-C_{12})$cycloalkyl, where alkyl can be straight or branched;

comprising contacting a compound of Formula III:

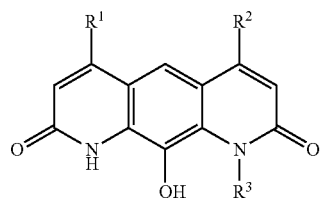

(III)

wherein $R^1$, $R^2$, and $R^3$ are as defined for Formula I;
with a dihaloalkane in the presence of a base and a suitable solvent to provide the compound of Formula I.

18. The method of claim 17 wherein the dihaloalkane is dibromomethane or 1,1-dibromoethane.

* * * * *